(12) United States Patent
Borsadia

(10) Patent No.: US 12,653,794 B2
(45) Date of Patent: *Jun. 16, 2026

(54) DEXTROMETHORPHAN TRANSDERMAL DELIVERY DEVICE

(71) Applicant: SHINKEI THERAPEUTICS, INC., Princeton, NJ (US)

(72) Inventor: Suresh Borsadia, Plainsboro, NJ (US)

(73) Assignee: SHINKEI THERAPEUTICS, INC.

( * ) Notice: Subject to any disclaimer, the term of this patent is extended or adjusted under 35 U.S.C. 154(b) by 0 days.

This patent is subject to a terminal disclaimer.

(21) Appl. No.: 18/381,849

(22) Filed: Oct. 19, 2023

(65) Prior Publication Data

US 2024/0189252 A1 Jun. 13, 2024

Related U.S. Application Data

(62) Division of application No. 17/858,471, filed on Jul. 6, 2022, now abandoned, which is a division of (Continued)

(51) Int. Cl.
*A61K 9/70* (2006.01)
*A61K 31/485* (2006.01)

(52) U.S. Cl.
CPC .......... *A61K 9/7061* (2013.01); *A61K 9/7069* (2013.01); *A61K 31/485* (2013.01)

(58) Field of Classification Search
None
See application file for complete search history.

(56) References Cited

U.S. PATENT DOCUMENTS 5,206,248 A 4/1993 Smith
5,626,866 A 5/1997 Ebert et al.
(Continued)

FOREIGN PATENT DOCUMENTS

JP H04-297415 10/1992
JP 2000-509037 7/2000
(Continued)

OTHER PUBLICATIONS

Nguyen et al . Dextromethorphan: an update on its utility for neurological and neuropsychiatric disorders. (Pharmacoloy & Therpaeutics, 2016, vol. 159:1-22). (Year: 2016).*

(Continued)

*Primary Examiner* — Bethany P Barham
(74) *Attorney, Agent, or Firm* — NIXON & VANDERHYE, PC

(57) ABSTRACT

Provided herein are transdermal delivery devices comprising dextromethorphan. The transdermal delivery device can be characterized by the novel design, for example, with an adhesive layer and a reservoir layer, with an adhesive layer comprising a mixture of two adhesives, and/or with a skin permeation enhancer, e.g., in an amount that can significantly enhance the flux of dextromethorphan. The transdermal delivery device can also be characterized by its in vitro and/or in vivo release profile, for example, that can provide a desired pharmacokinetic profile described herein. Also provided herein are methods of administering dextromethorphan, and methods of treating a disease or disorder described herein, using the transdermal delivery device herein.

8 Claims, 7 Drawing Sheets

Figure 1:
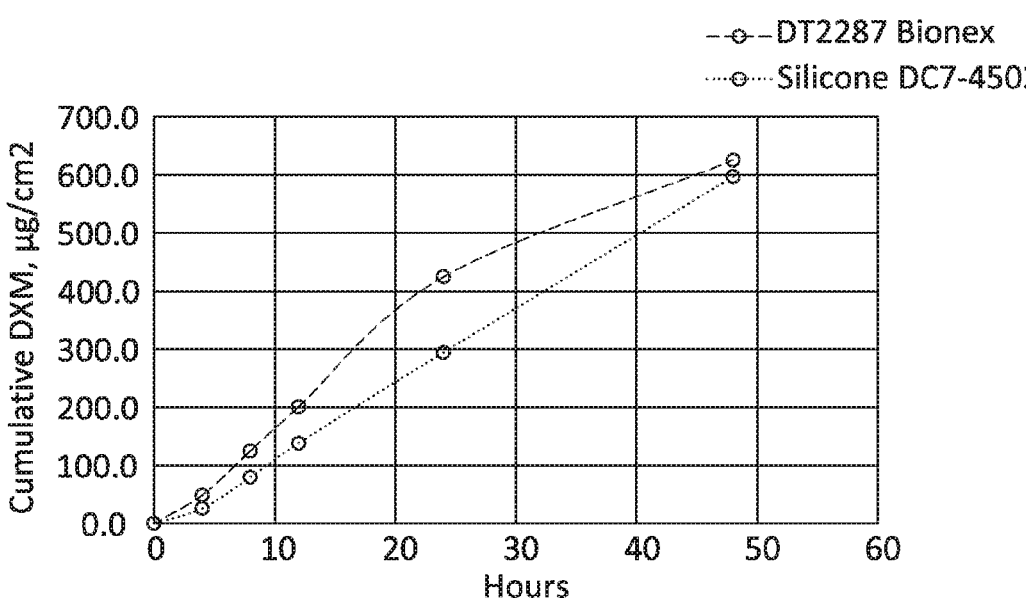

Related U.S. Application Data application No. 16/753,471, filed as application No. PCT/US2018/054178 on Oct. 3, 2018, now Pat. No. 11,382,869.

(60) Provisional application No. 62/680,182, filed on Jun. 4, 2018, provisional application No. 62/568,028, filed on Oct. 4, 2017.

(56) References Cited

U.S. PATENT DOCUMENTS

| | | | |
|---|---|---|---|
| 5,985,317 | A | 11/1999 | Venkateshwaran et al. |
| 6,335,030 | B1 * | 1/2002 | Hoeck .................. A61K 9/7053 |
| | | | 424/443 |
| 8,227,484 | B2 | 7/2012 | Yakatan et al. |
| 8,580,891 | B2 * | 11/2013 | Liu ......................... C09J 133/00 |
| | | | 525/100 |
| 11,382,869 | B2 * | 7/2022 | Borsadia .............. A61K 31/485 |
| 2004/0126323 | A1 * | 7/2004 | Shevchuk ............ A61K 9/7069 |
| | | | 424/10.1 |
| 2006/0223786 | A1 * | 10/2006 | Smith .................. A61K 31/137 |
| | | | 514/649 |
| 2007/0248657 | A1 | 10/2007 | Smith et al. |
| 2010/0311697 | A1 * | 12/2010 | Went ....................... A61P 25/00 |
| | | | 514/297 |
| 2011/0039875 | A1 | 2/2011 | Singh |
| 2012/0053169 | A1 | 3/2012 | Thomas |
| 2013/0137714 | A1 | 5/2013 | Berg |
| 2016/0038464 | A1 | 2/2016 | Tabuteau |
| 2016/0113908 | A1 | 4/2016 | Deshmukh et al. |

FOREIGN PATENT DOCUMENTS

| | | |
|---|---|---|
| JP | 2009-525343 | 7/2009 |
| JP | 2016-535786 | 11/2016 |
| RU | 2341265 C2 | 12/2008 |
| WO | WO 96/08229 A2 | 3/1996 |
| WO | WO 97/39742 A1 | 10/1997 |
| WO | WO 2007/092329 A2 | 8/2007 |
| WO | WO 2010/005507 A1 | 1/2010 |
| WO | 2015069809 A1 | 5/2015 |
| WO | WO 2019/070864 A1 | 4/2019 |
| WO | WO 2019/209940 A1 | 10/2019 |

OTHER PUBLICATIONS

International Search Report for PCT/US2018/054178 dated Jan. 24, 2019, 4 pages.

Written Opinion of the ISA for PCT/US2018/054178 dated Jan. 24, 2019, 7 pages.

Kristensen, "Simultaneous determination of dextromethorphan and its metabolites in human plasma by capillary electrophoresis", Elsevier, Journal of Pharmaceutical and Biomedical Analysis, vol. 18 (1998), pp. 827-838, 12 pages.

U.S. Appl. No. 17/915,687, filed Sep. 29, 2022, Borsadia et al., related application.

Martin Paspe Cruz, PharmD, CGP, BCPP, "Nuedexta for the Treatment of Pseudobulbar Affect", Drug Forecast, vol. 38, No. 6, Jun. 2013, P&T, pp. 325-328.

* cited by examiner

Top Layer

Reservoir Layer

Bottom Layer

A —■— Nuedexta BID for 7 days
B —●— Daily dose of 45 cm2

A —■— Nuedexta BID for 7 days
B —●— Daily dose of 90 cm2
C —▲— Daily dose of 60 cm2

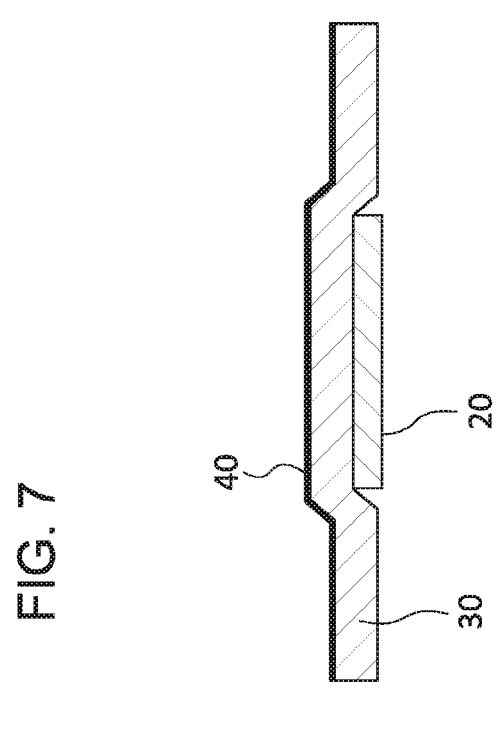
FIG. 7
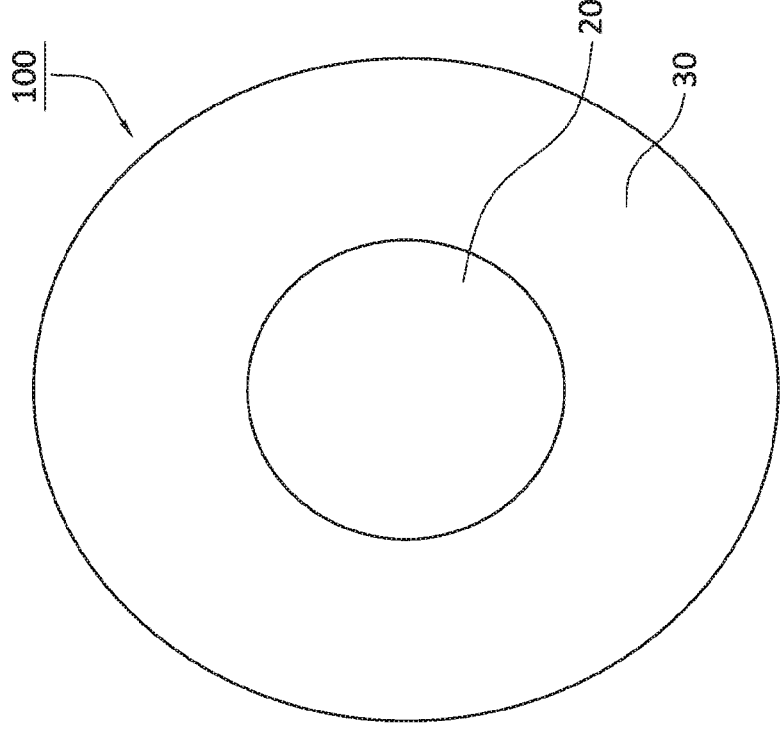

DEXTROMETHORPHAN TRANSDERMAL DELIVERY DEVICE

CROSS REFERENCE TO RELATED APPLICATIONS

This application is a divisional of U.S. application Ser. No. 17/858,471, filed Jul. 6, 2022, which is a divisional of U.S. application Ser. No. 16/753,471, filed Apr. 3, 2020, which is a U.S. National Phase of PCT/US2018/054178, filed Oct. 3, 2018, which claims benefit to U.S. Provisional Application Nos. 62/568,028, filed Oct. 4, 2017, and 62/680, 182, filed Jun. 4, 2018, the content of each of which is herein incorporated by reference in its entirety.

BACKGROUND OF THE INVENTION

Field of the Invention

In various embodiments, the present invention generally relates to transdermal delivery devices comprising dextromethorphan, and methods of preparing and uses thereof, for example, for use in treating a disease or disorder such as a neurological disease.

Background Art

NUEDEXTA® (dextromethorphan hydrobromide and quinidine sulfate) capsules, 20 mg/10 mg is a combination product containing dextromethorphan hydrobromide (an uncompetitive N-methyl-D-aspartate [NMDA] receptor antagonist and sigma-1 agonist) and quinidine sulfate (a CYP450 2D6 inhibitor). This product is indicated for the treatment of pseudobulbar affect (PBA). Dextromethorphan hydrobromide is the pharmacologically active ingredient of NUEDEXTA® that acts on the central nervous system (CNS). Quinidine sulfate is a specific inhibitor of CYP2D6-dependent oxidative metabolism used in NUEDEXTA® to increase the systemic bioavailability of dextromethorphan.

The recommended starting dose of NUEDEXTA® (dextromethorphan hydrobromide and quinidine sulfate) capsules, 20 mg/10 mg is one capsule daily by mouth for the initial seven days of therapy. On the eighth day of therapy and thereafter, the daily dose should be a one capsule every 12 hours for a total of two capsules daily. The need for continued treatment should be reassessed periodically, as spontaneous improvement of PBA occurs in some patients.

The most common adverse reactions (incidence of ≥3% and two-fold greater than placebo) in patients taking NUE-DEXTA® in descending order are diarrhea, dizziness, cough, vomiting, asthenia, peripheral edema, urinary tract infection, influenza, increased gamma glutamyltransferase, and flatulence. The following adverse reactions have been reported with the use of the individual component dextromethorphan: drowsiness, dizziness, nervousness or restlessness, nausea, vomiting, and stomach pain.

BRIEF SUMMARY OF THE INVENTION

In various embodiments, the present invention is directed to novel transdermal delivery devices comprising dextromethorphan, pharmaceutical compositions comprising dextromethorphan, and methods of administering dextromethorphan transdermally. The transdermal delivery devices, pharmaceutical compositions, and methods herein are useful in treating various diseases and disorders such as neurological diseases or disorders (e.g., PBA).

The transdermal delivery devices herein are novel in various aspects. In some embodiments, the transdermal delivery device can be characterized by a patch design, for example, having an adhesive layer and a reservoir layer. Typically, the reservoir layer can comprise a concentration of dextromethorphan at least 10% by weight of the reservoir layer. In some embodiments, the transdermal delivery device can be characterized by an adhesive layer comprising a mixture of two adhesives, such as a mixture of an acrylate adhesive and a silicone adhesive. In some embodiments, the transdermal delivery device can be characterized by having a skin permeation enhancer, for example, that can provide a higher flux compared to an otherwise equivalent transdermal delivery device without the skin permeation enhancer. In some embodiments, the transdermal delivery device can be characterized by having certain specific release profiles, such as in vitro flux profiles when tested using human cadaver skin and/or in vivo release profiles. In any of the embodiments described herein, the transdermal delivery device can be configured to provide one or more in vitro release profile and/or one or more PK profiles described herein in a user. In some embodiments, the transdermal delivery device can provide a pharmacokinetic ("PK") profile with a pharmaceutically effective plasma concentration of dextromethorphan in a subject in need thereof (e.g., subject having PBA) for a desired period of time. In some embodiments, the transdermal delivery device can be configured for use once daily, e.g., to provide a daily dose of dextromethorphan about 2 mg to about 50 mg. In some embodiments, the transdermal delivery device can be configured for use once in at least one day, for example, once in two days or more (e.g., once a week), or 1, 2, 3, 4, 5, or 6 times a week, e.g., to provide a daily dose of dextromethorphan about 2 mg to about 50 mg. Any of these features/aspects can be combined with the others and such combinations are specifically contemplated by the present disclosure.

In some embodiments, the transdermal delivery device can comprise an adhesive layer comprising an adhesive, which optionally comprises dextromethorphan dispersed in the adhesive in an amount of about 2% to about 12% by weight of the adhesive layer; and a reservoir layer comprising dextromethorphan in an amount of at least 10% (e.g., about 20% to about 60%) by weight of the reservoir layer. In some embodiments, the transdermal delivery device can comprise an adhesive layer comprising dextromethorphan dispersed in an adhesive comprising an acrylate adhesive and a silicone adhesive, wherein the weight ratio of the acrylate adhesive to silicon adhesive can range for example from about 20:1 to about 1:20. In some embodiments, the transdermal delivery device can comprise an adhesive layer comprising dextromethorphan dispersed in an adhesive, wherein the adhesive layer comprises a skin permeation enhancer, for example, in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

In some embodiments, the present disclosure provides a method of administering dextromethorphan to a subject (e.g., human subject) in need thereof. In some embodiments, the method comprises applying a transdermal delivery device to the skin of the subject. In some embodiments, the applying results in one or more PK profiles described herein.

In some embodiments, the transdermal delivery device is configured to have a flux characteristic such that the applying transdermally delivers dextromethorphan about 2 mg/day to about 50 mg/day to the subject. In some embodiments, the transdermal delivery device comprises an adhesive layer, wherein the adhesive layer comprises dextromethorphan dispersed in an adhesive, and a skin permeation enhancer, wherein the skin permeation enhancer is in an amount such that the applying results in a mean cumulative dextromethorphan permeated at 24 hours post application of at least about 25% (e.g., about 25%, about 50%, about 100%, about 150%, about 200%, or any ranges between the recited value) higher than that from applying an otherwise equivalent transdermal delivery device without the skin permeation enhancer. In some embodiments, the transdermal delivery device is applied once daily. In some embodiments, the transdermal delivery device is applied once in at least one day, e.g., once a week, twice a week, or three times a week.

In some embodiments, the present disclosure provides a method of treating a disease or disorder (e.g., a neurological disease or disorder such as PBA) in a subject (e.g., human subject) in need thereof. In some embodiments, the method comprising applying a transdermal delivery device comprising dextromethorphan to the skin of the subject, wherein the applying results in one or more of the PK profile described herein. In some embodiments, the transdermal delivery device is applied once daily. In some embodiments, the transdermal delivery device is applied once in at least one day, e.g., once a week, twice a week, or three times a week.

The methods herein are not limited to a particular subject or a particular class of subjects. In some embodiments, the subject is characterized as an extensive metabolizer. In some embodiments, the subject is characterized as a poor metabolizer. In some embodiments, the subject is not co-administered a CYP2D6 inhibitor. In some embodiments, the subject is not co-administered quinidine. In some embodiments, the subject is co-administered a CYP2D6 inhibitor such as quinidine, bupropion, etc. However, in any of the embodiments described herein, the subject does not suffer from a cough and/or does not need an antitussive.

In some embodiments, the methods herein can further comprise administering to the subject an active agent other than dextromethorphan. For example, in some embodiments, the method comprises administering to the subject an antidepressant. In some embodiments, the method described herein further comprises administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof. These additional agents can be administered simultaneously or sequentially, via the same or different route.

BRIEF DESCRIPTION OF THE DRAWINGS/FIGURES

FIG. 1 presents graphs showing in vitro flux study results for transdermal delivery device with Formulations A and B with different adhesives, the flux of dextromethorphan (DXM) from the patch with Formulation A (acrylate adhesive) is shown on the top with a faster flux than the patch with Formulation B (silicone adhesive).

Figure 2:
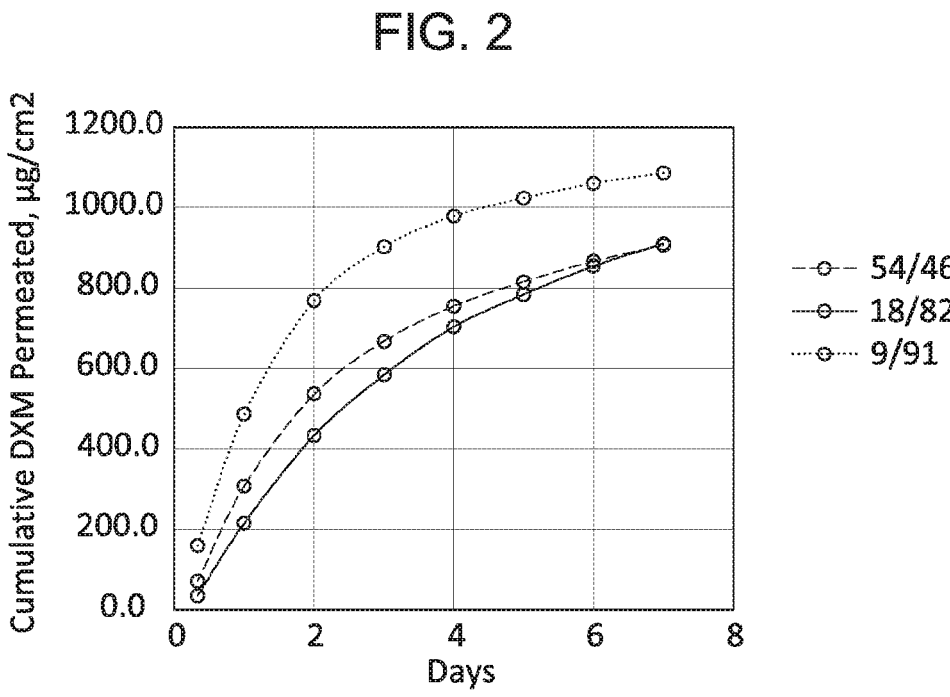

FIG. 2 presents graphs showing in vitro flux study results for patches with Formulations C1-C3, which contains different ratios of silicone adhesive to acrylic adhesive, 54:46 (middle), 18:92 (bottom), and 9:91 (top).

Figure 3:
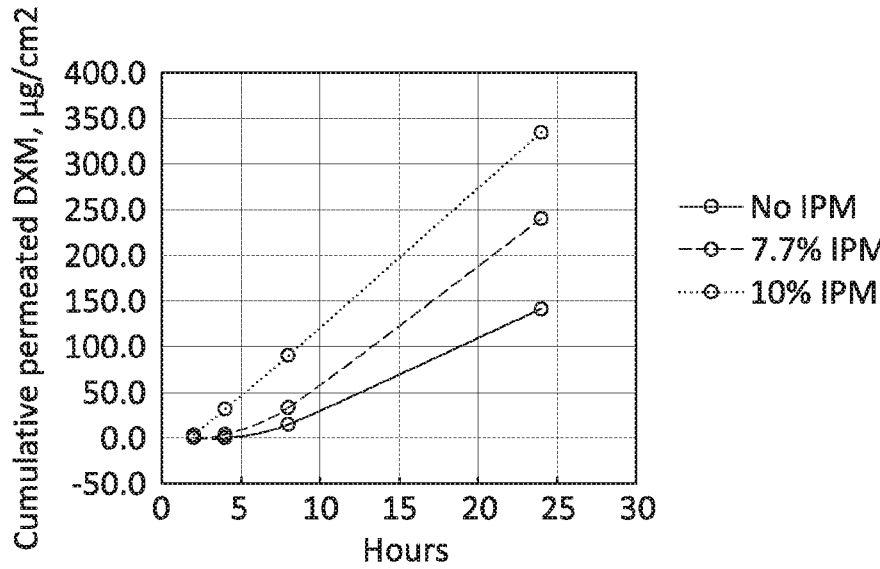

FIG. 3 presents graphs showing effects of a skin permeation enhancer (isopropyl myristate, IPM) on in vitro flux: 10% IPM (top), 7.7% IPM (middle), and 0% IPM (bottom).

Figure 4A:
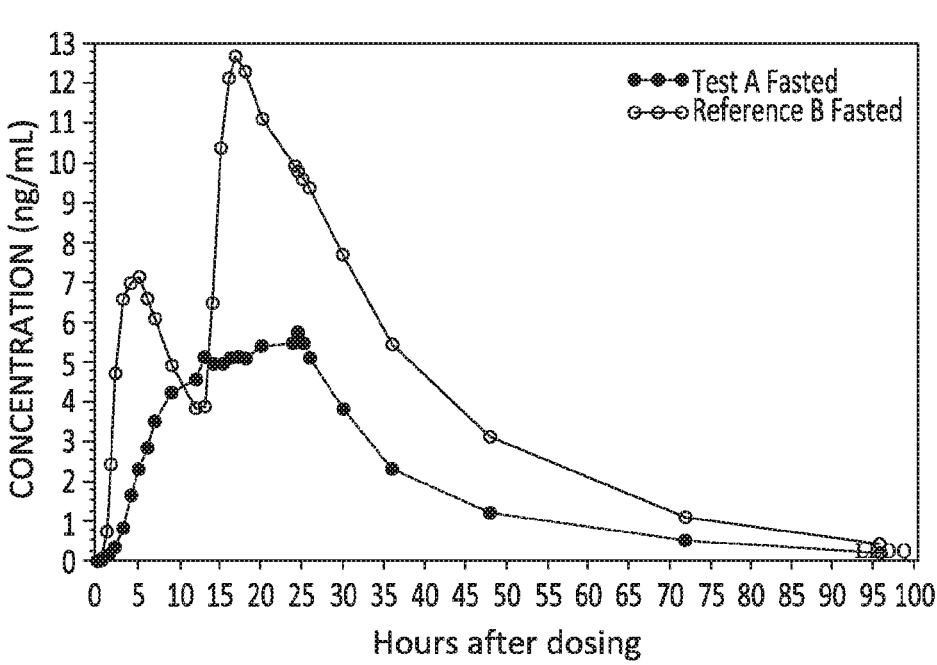
Figure 4B:
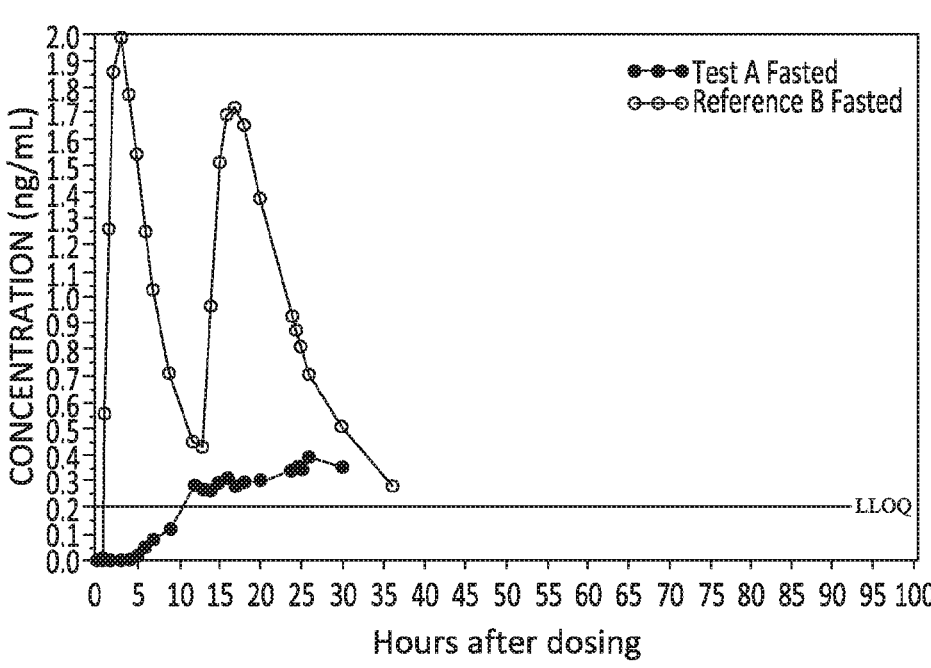

FIG. 4A shows dextromethorphan plasma concentration over the course of 96 hours for a human clinical study comparing the effect of administration of DXM transdermal patch (test A) for 24 hours and oral administration of Neudexta (20 mg DXM/10 mg quinidine) (Reference B) twice a day. FIG. 4B shows the metabolite, dextrorphan's plasma concentration over the course of 96 hours for the same study. For FIGS. 4A and 4B, both test and reference administration were to subject under fasted condition. The plasma concentrations refer to mean plasma concentrations, with N=16.

Figure 5:
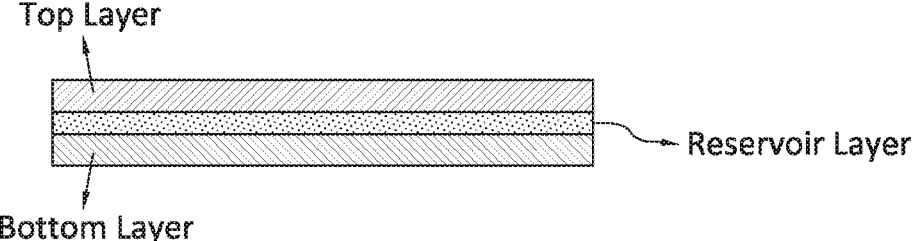

FIG. 5 shows a multilayer patch design. The top layer is a skin-contacting adhesive layer, the middle layer is a reservoir layer, and the bottom layer is a backing layer or an adhesive layer, which can be the same or different from the top layer.

Figure 6A:
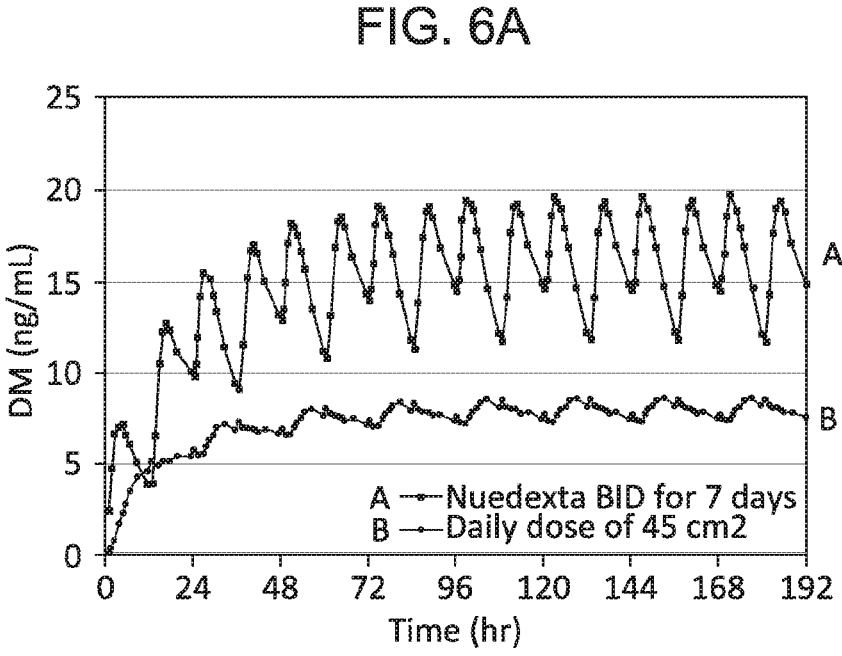
Figure 6B:
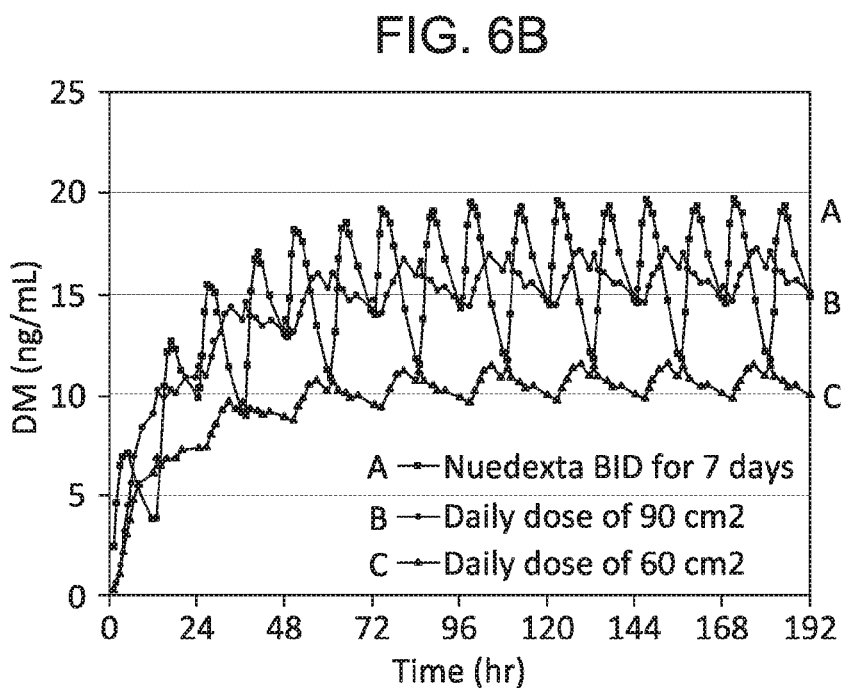

FIGS. 6A and 6B show simulated plasma concentrations of dextromethorphan over time following administration of DXM transdermal patches, 45 cm$^2$ (FIG. 6A), 60 cm$^2$ (FIG. 6B), or 90 cm$^2$ patch (FIG. 6B), once daily for 7 days. The plasma concentrations of dextromethorphan (DM) over time following oral administration of Neudexta (20 mg DXM/10 mg quinidine) twice a day for 7 days are also shown for comparison.

Figures 6C, 6D:
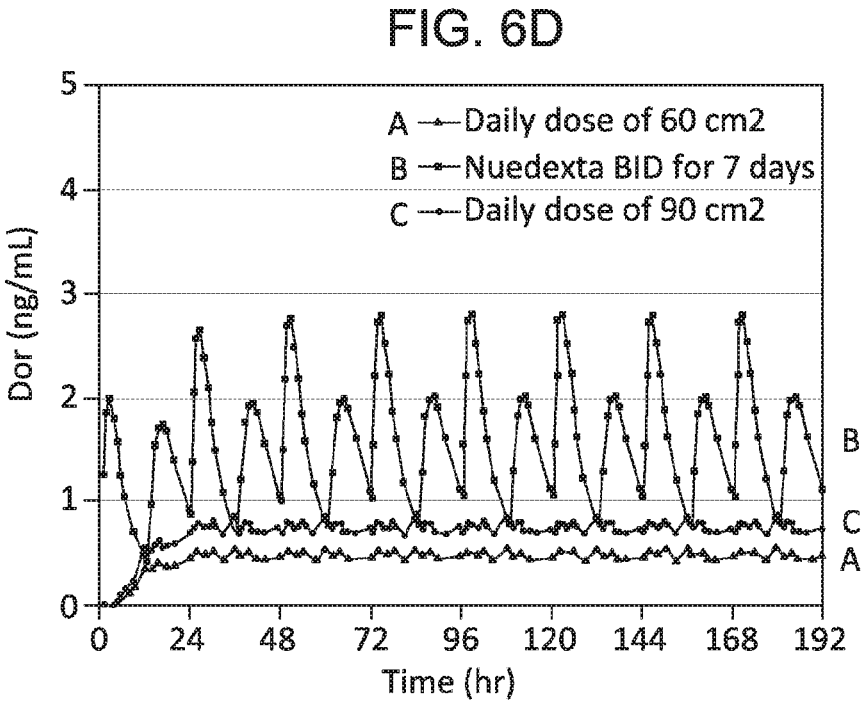

FIGS. 6C and 6D show simulated plasma concentrations of dextrorphan (Dor) over time following administration of DXM transdermal patches, 45 cm$^2$ (FIG. 6C), 60 cm$^2$ (FIG. 6D), or 90 cm$^2$ patch (FIG. 6D), once daily for 7 days. The plasma concentrations of dextrorphan over time following oral administration of Neudexta (20 mg DXM/10 mg quinidine) twice a day for 7 days are also shown for comparison.

FIG. 7 shows a two-zone patch design.

DETAILED DESCRIPTION OF THE INVENTION

The unpredictability of transdermal administration is notorious. In the inventor's experience, testosterone can be delivered transdermally without enhancer at a rate three orders of magnitude higher than for beta estradiol. Structurally and by calculated Log P, these compounds are very similar, such that this difference could not be anticipated. See, U.S. Provisional Appl. No. 62/568,028, filed Oct. 4, 2017, the content of which is incorporated by reference in its entirety.

Dextromethorphan (DXM) has been used orally to treat neurological disorders such as pseudobulbar affect (PBA), emotional lability, agitation in Alzheimer's, major depressive disorder, treatment resistant disorder, pain management, other CNS disorders, and the like. But, to be effective, it must be delivered with a substance that competitively inhibits the liver enzyme cytochrome P450 2D6 (CYP2D6). It particular, this has meant it is co-administered with quinidine. Otherwise, too little makes it pass the liver's diligence of digested food. U.S. Pat. No. 6,335,030 B1 describes some examples of dextromethorphan patches. No pharmacokinetic data on transdermal administration of dextromethorphan was known.

As detailed herein, the present disclosure first shows that dextromethorphan can be delivered transdermally in a therapeutically effective amount. Transdermally delivering dextromethorphan can be advantageous in many different aspects. For example, because the transdermal route avoids first-pass metabolism, the transdermal delivery devices herein can be administered to achieve therapeutically effective plasma concentration without regard to whether a CYP2D6 inhibitor such as quinidine is co-administered. As such, the transdermal delivery device and methods herein can be administered to transdermally deliver dextromethorphan to subjects who are for example, sensitive or intolerant to CYP2D6 inhibitors such as quinine (e.g., having one or more side effects associated with quinidine, or is co-administered a drug whose metabolism is affected by CYP2D6 inhibitors such as quinidine). Further, the transdermal delivery device and methods herein can be conveniently administered to transdermally deliver dextromethorphan to a subject without regard to, e.g., with/without first determining, whether the subject is a poor metabolizer, an intermediate metabolizer, or an extensive metabolizer of dextromethorphan. For brevity, as used herein, unless otherwise obvious from context, poor metabolizer (PM), intermediate metabolizer (IM), or extensive metabolizer (EM) refers to the subject's ability to metabolize dextromethorphan. Categorization of a subject as a PM, IM, or EM (alternatively labeled as ultrametabolizers or ultrarapid metabolizers or UM) is known in the art. See e.g., Treducu A. L. D. et al. *Frontiers in Pharmacology, vol. 9, Article* 305 (April 2018), which based on genotype assigned subjects as UM if containing "≥3 normal function gene copies").

Further, unexpectedly, administering the transdermal delivery devices herein can provide a longer $T_{1/2}$ of dextromethorphan, a reduced amount of metabolite (evidenced by the higher ratio of dextromethorphan to dextrophan), and/or a lower peak to trough ratio, when compared to the corresponding parameters observed from oral administration of Neudexta. These characteristics can provide superior clinical experience compared to Neudexta, for example, with more accurate dosing, less frequent dosing, and reduced potential for side effects. The transdermal delivery devices herein can also be configured as a one day patch, 2-day patch, 3-day patch, 4-day patch, 5-day patch, 6-day patch, or 7-day patch, which is suitable for dosing frequencies ranging from once a day to once a week, for example, once in more than 24 hours, more than 36 hours, more than 48 hours, etc., or 1, 2, 3, 4, 5, or 6 times a week. Thus, using the transdermal delivery devices herein can provide improved patient compliance, at least by avoiding the twice-a-day dosing regimen of Neudexta.

Transdermal Delivery Device Comprising Dextromethorphan

Certain embodiments of the present disclosure are directed to novel transdermal delivery devices comprising dextromethorphan.

Various patch designs can be used for the transdermal delivery device herein. The transdermal delivery device herein typically comprises a backing layer, an adhesive layer (e.g., a drug-in-adhesive layer), which is the skin-contacting layer when in use, and optionally a reservoir layer. The adhesive layer typically comprises dextromethorphan dispersed (e.g., homogenously dispersed, which also includes dissolved) in an adhesive, preferably a pressure sensitive adhesive. More than one adhesive layers can be used for the transdermal delivery device herein. The adhesive layer is typically formulated such that the transdermal delivery device can adhere to the skin of a user for a desired period of time. For example, in some embodiments, the transdermal delivery device is capable of adhering continuously to the skin of a user for about 8 hours, about 12 hours, about 18 hours, about 24 hours, about 2 days, about 3 days, about 4 days, about 5 days, about 6 days, or about 7 days or more.

In some embodiments, the transdermal delivery device can be a drug-in-adhesive (DIA) patch. In some embodiments, the DIA patch is a single layer patch, for example, the single layer includes dextromethorphan homogenously dispersed in the adhesive. In some embodiments, the DIA patch is a multilayer patch. For example, two drug-in-adhesive layers can be included in the patch, which is optionally separated by a membrane, e.g., a rate-controlling membrane, or by a reservoir layer. In some embodiments, one of the drug-in-adhesive layer can be a reservoir layer, for example, with a higher dextromethorphan concentration than the other layer. In some embodiments, the two drug-in-adhesive layers can sandwich a reservoir layer.

A drug-in-reservoir (DIR) design can also be used for the transdermal delivery device herein. In some embodiments, the reservoir layer and the adhesive layer can be laminated to each other or separated, for example, by a rate-controlling membrane. For example, in some embodiments, the reservoir layer, such as a drug matrix, can be laminated with the adhesive layer. Those skilled in the art would understand that such adhesive layer can also contain certain amount of drug, for example, through equilibrium.

Other patch designs can also be used for the transdermal delivery device herein. For example, in some embodiments, the transdermal delivery device can be an active patch, such as an iontophoresis patch. In some embodiments, the transdermal delivery device can be a minimally invasive patch, such as a microneedle based patch.

The transdermal delivery device can include dextromethorphan as the only drug or in combination with another drug. Unless obviously contradictory, in any of the embodiments described herein, dextromethorphan can be the only drug in the transdermal delivery device. Dextromethorphan can exist in various forms, for example, as a free base or a pharmaceutically acceptable salt. As used herein, the weight percentage, concentration, flux, etc. regarding dextromethorphan should be understood as the total amount of dextromethorphan measured and/or calculated, with the value expressed in the equivalent value for dextromethorphan base. Further, all weight percentages, unless otherwise obvious from context, should refer to the weight percentage based on the final formulation (e.g., final adhesive layer or reservoir layer etc.) or transdermal delivery device as appropriate. In any of the embodiments described herein, the dextromethorphan can exist in its free base form, except that it can be protonated through equilibrium with other ingredient(s). For example, in any of the embodiments described herein, the transdermal delivery device or pharmaceutical compositions described herein can be prepared by mixing directly or indirectly the recited amount of dextromethorphan base with the other ingredients.

In any of the embodiments described herein, the dextromethorphan in the transdermal delivery device can be partially or completely replaced with a deuterated dextromethorphan, e.g., the d3 analog ($O$-$CD_3$, or $N$-$CD_3$) or d6 analog ($N$-$CD_3$,$O$-$CD_3$) see, e.g., claims 1 and 17 of U.S. Pat. No. 7,973,049, the content of which is incorporated by reference in its entirety. Apparently, in such embodiments, the methods using the deuterated dextromethorphan patches would provide deuterated dextromethorphan to the user. As used herein, a deuterated dextromethorphan refers to a compound resulted from substituting one or more hydrogen atoms of dextromethorphan with deuterium such that each substituted position has a deuterium content above the natural abundance, i.e., the substituted position is enriched with deuterium. In some embodiments, the deuterated dextromethorphan has at least one position with deuterium enriched to at least 10% deuterium, at least 50% deuterium, at least 90% deuterium, at least 95% deuterium or at least 98% deuterium. In any of the embodiments described herein, the dextromethorphan in the transdermal delivery device can also be partially or completely replaced with a dextromethorphan analog, such as a fluorinated dextromethorphan or a skin permeable prodrug of dextromethorphan, etc.

The adhesive layer typically includes a pressure sensitive adhesive (PSA). Useful features for pressure sensitive adhesive include adequate tack, good adhesion and cohesive strength. Further useful attributes include biocompatibility (e.g., non-irritating, non-sensitizing non-toxic), formulation compatibility, delivery system compatibility and the like. Useful pressure sensitive adhesive include for example polyacrylates, poly acrylic esters, silicones, polyisobutylenes and the like.

PSAs are generally known in the art. See, e.g., Tan et al., Pharm Sci & Tech Today, 2:60-69 (1999). Non-limiting useful PSAs include polyisobutylenes (PIB), silicone polymers, acrylate copolymers, and combinations thereof. In some embodiments, the pressure sensitive adhesive comprises a polyisobutylene adhesive, a silicone polymer adhesive, an acrylate copolymer adhesive, or a combination thereof. In some embodiments, the pressure sensitive adhesive comprises an acrylate copolymer adhesive. Non-limiting useful acrylate copolymers include, for example, acrylic pressure sensitive adhesives such as a poly acrylate vinyl acetate copolymer, e.g., Duro-Tak 87-2287, Duro-Tak 87-4098, Duro-Tak 87-4287, or Duro-Tak 87-2516, Duro-Tak 87-2852 or Duro-Tak 87-2194), which are manufactured by Henkel Adhesives. PIBs are elastomeric polymers that are commonly used in PSAs, both as primary-base polymers and as tackifiers. PIBs are homopolymers of isobutylene and feature a regular structure of a carbon-hydrogen backbone with only terminal unsaturation. Non-limiting useful PIBs include those marketed under the trade name Oppanol by BASF. The silicone polymers are a high molecular weight polydimethylsiloxane that contains residual silanol functionality (SiOH) on the ends of the polymer chains. Non-limiting useful silicone PSAs for use in pharmaceutical applications include those available from Dow Corning Corporation, for example under the trade name of BIO-PSA, e.g., BIO-7-4202. In some embodiments, the adhesive layer is about 0.1 mils to about 10 mils, e.g., about 1.5 mils to about 10 mils (e.g., about 1.5 mils to about 2 mils) thick.

In some embodiments, suitable adhesives include for example the following silicone adhesives from Dow Corning: BIO-PSA 7-410X, BIO-PSA 7-420X, BIO-PSA 7-430X, BIO-PSA 7-440X, BIO-PSA 7-450X, BIO-PSA 7-460X, and BIO-PSA Hot Melt Adhesive. In some embodiments, suitable adhesives include for example the following polyacrylate/poly acrylic ester adhesives from Henkel Adhesives: Duro-Tak 87-900A, 87-9301, 87-4098, 87-2510, 87-2287, 87-4287, 87-2516, 87-2074, 87-235A, 87-2353, 87-2852, 87-2051, 87-2052, 87-2054, 87-2194, 87-2196, 87-6908, 387-2510, 387-2287, 387-2516, 387-2353, 387-2051, 387-2051 and 387-2054, GELVA GMS 3083, 3253, 788 and 9073. These can for example have hydroxy functional groups, carboxylic groups, hydroxy and carboxylic groups, or no functional groups (as active as the foregoing). These can for example include vinyl acetate monomer, or not.

Typically, the transdermal delivery device (e.g., a DIA patch) is supported by a backing layer such as an impermeable backing film, and the adhesive surface is protected by a release liner prior to use. Various materials can be used as a backing layer for the transdermal delivery device herein. Typically, the backing layer is impermeable. For example, the backing layer can be comprised of impermeable polymeric films such as polyester (PET) or polyethylene (PE) films. In some embodiments, the backing layer can comprise a polyester, such as Scotchpak 9736 or Scotchpak 1012, a polyurethane film, such as Scotchpak 9701, or a polyethylene film, such as CoTran 9720. In some embodiments, the backing is part of an overlay, and can be a non-woven fabric, a polyurethane film, or other pliable material to provide flexibility and better wear.

The release liner can be manufactured in the desired size for the present invention. The release liner can be comprised of silicone or fluoro-polymer coated polyester film. The release liner protects the transdermal delivery device during storage and is removed before its use. Silicone-coated release liners include those manufactured by Mylan Corporation, Loparex Corporation, and 3M's Drug Delivery Systems. The fluoro-polymer coated release liners include those manufactured and supplied by 3M's Drug Delivery Systems and Loparex. In some embodiments, the release liner comprises 3M's ScotchPak 9744 or Scotchpak 1022.

The transdermal delivery devices herein can also optionally include other suitable excipients such as humectants, plasticizers, antioxidants, anti-irritants, gel-forming agents, crystallization inhibitors, drug release modifiers etc. These excipients are within the knowledge of those skilled in the art, and can be found, for example, in the Handbook of Pharmaceutical Excipients, ($7^{th}$ ed. 2012), the entire content of which is hereby incorporated by reference. In some embodiments, additional active ingredient(s) can also be included in the transdermal delivery device herein.

The transdermal delivery devices (e.g., DIA patches) herein can have different sizes (patch sizes) depending on its application. Typically, the patch sizes can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120 $cm^2$, about 150 $cm^2$ about 200 $cm^2$ or any ranges between the specified values), for example, about 10 $cm^2$ to about 100 $cm^2$.

When applying the transdermal delivery devices (e.g., DIA patches) herein to a skin of a subject, all of the adhesive surface can become in contact with the skin in theory. Thus, the area of the adhesive surface defines a skin contact area, which is also referred herein to as an active surface area. In some embodiments, the adhesive surface is the only surface of the transdermal delivery device that is in contact with the skin upon application, and the active surface area is the same as the area of the adhesive surface. In some embodiments, the adhesive surface and one or more other surfaces of the transdermal delivery device are in contact with the skin upon application, and the entire skin contact area is the active surface area. In a typical DIA patch, the patch size is the same as the active surface area. Unless otherwise obvious from context, the unit "/$cm^2$" should be understood as per square centimeter of active surface area as defined herein.

The active surface area can determine the doses of the drug to be delivered. Typically, the active surface area can be about 5 $cm^2$ to about 300 $cm^2$ (e.g., about 5 $cm^2$, about 10 $cm^2$, about 20 $cm^2$, about 30 $cm^2$, about 40 $cm^2$, about 50 $cm^2$, about 60 $cm^2$, about 80 $cm^2$, about 100 $cm^2$, about 120

$cm^2$, about 150 $cm^2$, about 200 $cm^2$ or any ranges between the specified values), for example, about 10 $cm^2$ to about 100 $cm^2$.

In some embodiments, the transdermal delivery device herein can be configured to provide dextromethorphan to a user at least about 2 mg/day (e.g., about 2 mg/day to about 50 mg/day) for a period of time of 1 day or more, for example, 2 days, 3 days, 4 days, 5 days, 6 days, or 7 days. For example, in some embodiments, the transdermal delivery device is configured to transdermally deliver dextromethorphan to a user about 5 mg/day to about 50 mg/day (e.g., about 5 mg/day, about 10 mg/day, about 20 mg/day, about 30 mg/day, about 40 mg/day, about 50 mg/day, or any ranges between the recited values) for 1 day or more (e.g., 1.5 days, 2 days, 3 days, 4 days, 5 days, 6 days, 7 days, or any ranges between the recited values).

The total dextromethorphan loading for the transdermal delivery device can be adjusted based on the desired total dose. Typically, the total dextromethorphan loading exceeds 0.5 $mg/cm^2$ (e.g., at least 2 $mg/cm^2$, at least 3 $mg/cm^2$, at least 4 $mg/cm^2$, at least 5 $mg/cm^2$, at least 6 $mg/cm^2$, etc.). For example, in some embodiments, the transdermal delivery device can have a total dextromethorphan loading of about 0.5 $mg/cm^2$ to about 8 $mg/cm^2$, e.g., about 2 $mg/cm^2$ to about 6 $mg/cm^2$ (e.g., about 2 $mg/cm^2$, about 3 $mg/cm^2$, about 4 $mg/cm^2$, about 5 $mg/cm^2$, about 6 $mg/cm^2$, or any ranges between the recited values). As used herein, the total dextromethorphan loading of a patch can be calculated by dividing the total amount of the dextromethorphan in the patch by the patch's active surface area.

TDD with a Reservoir Layer

In some embodiments, a reservoir layer can be optionally included in the transdermal delivery device herein. For example, for high daily doses and/or application for an extended period of time (e.g., 1 day or more), the reservoir layer can provide more sustained flux of dextromethorphan to a user.

In some embodiments, the transdermal delivery device comprises an adhesive layer comprising an adhesive and a reservoir layer comprising dextromethorphan. In some embodiments, the adhesive layer optionally comprises dextromethorphan dispersed in the adhesive. In some embodiments, the adhesive layer does not include dextromethorphan, other than through equilibrium with the reservoir layer. In some embodiments, the adhesive layer comprises dextromethorphan dispersed in the adhesive. In some embodiments, the reservoir layer comprises dextromethorphan in an adhesive. In some embodiments, the reservoir layer and the adhesive layer are the same layer. In some embodiments, the reservoir layer is sandwiched between the adhesive layer and a backing layer. In some embodiments, the reservoir layer can be sandwiched between two adhesive layers which can be the same or different. For example, in some embodiments, the two adhesive layers can have the same ingredients with the same concentrations, and in some embodiments, can also have the same thickness. However, in some embodiments, the two adhesive layers can have different ingredients, or same ingredients with different concentrations, or have different thickness, etc. An exemplary configuration can be seen in FIG. 3, where the adhesive layer is the top layer, and the backing layer or an adhesive layer, which can be the same as or different from the top layer, is the bottom layer, and the reservoir layer is the middle layer.

In some embodiments, the reservoir layer is separated from the adhesive layer by a membrane, e.g., a rate controlling membrane such as a microporous membrane. The reservoir layer preferably contains an adhesive; however, other designs of the reservoir layer are also suitable when compatible with the adhesive layer and the backing layer. For example, in some embodiments, the reservoir layer can be a scrim/nonwoven fabric saturated with dextromethorphan, or having dextromethorphan dispersed in other suitable carrier/substrate.

Dextromethorphan can be included in the adhesive layer and reservoir layer in various concentrations. Typically, the concentration of dextromethorphan in the reservoir layer is higher than that in the adhesive layer. For example, in some embodiments, the adhesive layer can comprise dextromethorphan in an amount of about 2% to about 12% (e.g., about 2%, about 4%, about 6%, about 8%, about 10%, about 12%, or any range between the recited values) by weight of the adhesive layer; whereas the reservoir layer can comprise dextromethorphan in an amount of about 20% or more, for example, about 30% or more, about 40% or more, about 50% or more, such as about 20% to about 60%, about 30% to about 50%, by weight of the reservoir layer. In some embodiments, the adhesive layer comprises dextromethorphan in an amount of about 6% to about 12% (e.g., about 6%, about 7%, about 8%, about 9%, about 10%, about 11%, about 12%, or any ranges between the recited values) by weight of the adhesive layer. In some embodiments, the adhesive layer comprises dextromethorphan at or near the saturation concentration in the adhesive, for example, about 10% by weight in an acrylate adhesive. In some embodiments, the reservoir layer comprises dextromethorphan above the saturation concentration in the adhesive. In other words, the dextromethorphan in the reservoir layer is oversaturated and can therefore contain solid dextromethorphan, which can serve as a drug depot.

Suitable adhesives for the adhesive layer and the reservoir layer, as applicable, include any of those described herein, preferably pressure sensitive adhesives. The adhesives included in the adhesive layer and reservoir layer can be the same or different. In some embodiments, the adhesives included in the adhesive layer and reservoir layer are the same, for example, acrylate based adhesives. Other suitable adhesives include a polyisobutylene adhesive, a silicone polymer adhesive, an acrylate copolymer adhesive (e.g., a poly acrylate vinyl acetate copolymer, such as Duro-Tak 87-2287), or a combination thereof. In any of the embodiments described herein, the adhesive layer can be configured for adhering to a user's skin continuous for at least 1 day (e.g., at least 2 days, at least 3 days, at least 4 days, at least 5 days, at least 6 days, at least 7 days).

The adhesive (e.g., a pressure sensitive adhesive) typically is the main ingredient for the adhesive layer and reservoir layer (as applicable). For example, in some embodiments, the adhesive layer comprises a pressure sensitive adhesive in an amount of about 50% to about 90% by weight of the adhesive layer. In some embodiments, the pressure sensitive adhesive is present in an amount of about 60% to about 85% (e.g., about 60%, about 70%, about 75%, about 80%, about 85%, or any ranges between the recited values) by weight of the adhesive layer. In some embodiments, the reservoir layer can include a pressure sensitive adhesive in an amount of about 20% to about 80% by weight of the reservoir layer. For example, in some embodiments, the pressure sensitive adhesive is present in an amount of about 20% to about 65% (e.g., about 20%, about 30%, about 35%, about 40%, about 50%, about 60%, about 65%, or any ranges between the recited values) by weight of the reservoir layer.

Suitable sizes for the transdermal delivery device are described herein. In some embodiments, the transdermal delivery device has an active surface area of about 5 cm$^2$ to about 200 cm$^2$. In some embodiments, the transdermal delivery device has an active surface area of about 10 cm$^2$ to about 150 cm$^2$. In some embodiments, the transdermal delivery device has an active surface area of about 30 cm$^2$ to about 100 cm$^2$ (e.g., about 30 cm$^2$, about 40 cm 2, about 50 cm$^2$, about 60 cm$^2$, about 70 cm$^2$, about 80 cm$^2$, about 90 cm$^2$, about 100 cm$^2$, or any ranges between the recited values).

The adhesive layer and reservoir layer can be of various thickness. For example, in some embodiments, the adhesive layer is about 0.1 mil to about 10 mils thick (e.g., about 0.5 mil to about 10 mils, about 1 mil to 10 mils). In some embodiments, the reservoir layer can also be about 0.1 mil to about 10 mils thick (e.g., about 0.5 mil to about 10 mils, about 1 mil to 10 mils).

Skin permeation enhancers can also be included in the adhesive layer and the reservoir layer. For example, in some embodiments, the adhesive layer comprises a skin permeation enhancer selected from isopropyl myristate, oleyl oleate, oleic acid, glycerol monooleate, other fatty acids and fatty acid esters with carbon chain lengths of $C_{12}$ to $C_{18}$, and combinations thereof. In some embodiments, the adhesive layer comprises isopropyl myristate. Similarly, in some embodiments, the reservoir layer comprises a skin permeation enhancer selected from isopropyl myristate, oleyl oleate, oleic acid, glycerol monooleate, other fatty acids and fatty acid esters with carbon chain lengths of $C_{12}$ to $C_{18}$, and combinations thereof. In some embodiments, the reservoir layer comprises isopropyl myristate.

Various amounts of skin permeation enhancers can be used for the adhesive layer and the reservoir layer. Typically, the skin permeation enhancer can be present in an amount of about 2% to about 15% by weight of the adhesive layer or reservoir layer. For example, in some embodiments, the skin permeation enhancer is present in an amount of about 6% to about 12% (e.g., about 6%, about 7%, about 8%, about 9%, about 10%, about 11%, about 12%, or any ranges between the recited values) by weight of the adhesive layer. In some embodiments, the skin permeation enhancer is present in an amount of about 6% to about 12% (e.g., about 6%, about 7%, about 8%, about 9%, about 10%, about 11%, about 12%, or any ranges between the recited values) by weight of the reservoir layer. However, in some embodiments, the adhesive layer and/or the reservoir layer can also be substantially free of a skin permeation enhancer selected from isopropyl myristate, oleyl oleate, oleic acid, glycerol monooleate, other fatty acids and fatty acid esters with carbon chain lengths of $C_{12}$ to $C_{18}$, and combinations thereof.

In some embodiments, the adhesive layer and/or the reservoir layer can include an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof. In some embodiments, the agent can be present in an amount of about 2% to about 20% (e.g., about 2%, about 2.5%, about 3%, about 4%, about 5%, about 6%, about 10%, about 15%, about 20%, or any ranges between the recited values) by weight of the adhesive layer or reservoir layer. Without wishing to be bound by theories, it is believed that such agents can improve the cohesive strength of the adhesive layer or reservoir layer. Further, such agents can have other functions such as inhibiting crystallization. In some embodiments, the adhesive layer comprises an agent effective for improving cohesive strength of the adhesive layer. In some embodiments, the reservoir layer comprises an agent effective for improving cohesive strength of the reservoir layer.

It should be noted that the identities of ingredients such as adhesives, skin permeation enhancers, agents, and amounts thereof, for the adhesive layer and the reservoir layer are independently selected, which can be the same or different. Typically, the amounts can vary whereas the identity can be the same. The thickness of the adhesive layer and the reservoir layer can also be the same or different.

TDD with a Mixture of Adhesives

As detailed in the Examples section, varying the adhesive components can affect the flux characteristics of the transdermal delivery device comprising dextromethorphan. Thus, in some embodiments, the present disclosure also provides a transdermal delivery device comprising an adhesive layer, wherein the adhesive layer comprises two or more adhesives. Typically, the adhesive layer comprises dextromethorphan dispersed in the two or more adhesives.

In some embodiments, the adhesive layer can include a mixture of an acrylate copolymer adhesive (e.g., Durotak 87-2287) and a silicone adhesive (e.g., BIO-7-4202) in various ratios (e.g., a weight ratio of acrylate adhesive to silicone adhesive ranging from about 1:20 to about 20:1). In some embodiments, the weight ratio of the acrylate adhesive to silicon adhesive ranges from about 10:1 to about 1:10 (e.g., about 10:1, about 4:1, about 1:1, about 1:4, or any ranges between the recited value). Other ingredients and suitable amounts that can be optionally included in the adhesive layer, such as skin permeation enhancers, include those described herein.

The adhesive layer with two or more adhesives can be included/used in any of the transdermal delivery device herein. For example, in some embodiments, the transdermal delivery device comprising a reservoir layer described herein can have an adhesive layer with a mixture of an acrylate copolymer adhesive (e.g., Durotak 87-2287) and a silicone adhesive (e.g., BIO-7-4202) in various ratios.

TDD with a Skin Permeation Enhancer

Skin permeation enhancers (transdermal enhancers) can enhance the skin permeability of dextromethorphan through the skin and can be optionally included in the transdermal delivery device herein. Various skin permeation enhancers can be included. Non-limiting useful skin permeation enhancers include, for example, sulfoxides (e.g., dimethylsulfoxide, DMSO), Azones (e.g., laurocapram), pyrrolidones (e.g., 2-pyrrolidone, 2P), alcohols and alkanols (e.g., ethanol or decanol), esters, glycols (e.g., propylene glycol (PG)), surfactants (e.g., Tween 80), terpenes, and combinations thereof. See, e.g., Williams et al., Adv Drug Deliv Rev. 27; 56(5):603-18 (2004). In some embodiments, the permeation enhancer comprises one or more compounds chosen from sulfoxides, alcohols, alkanols, esters, glycols, and surfactants. In some embodiments, the permeation enhancer comprises one or more compounds chosen from dimethyl sulfoxide (DMSO), oleic alcohol, oleayl oleate, oleic acid, levulinic acid, other fatty acids and fatty-acid esters, propylene glycol, dipropylene glycol, ethanol, and surfactants such as Tween 80. In some embodiments, the transdermal device can include one or more compounds chosen from DMSO, N-methyl-2-pyrolidone, azone, myristic acid, sesquiterpene oil, 4-decyloxazolidin-2-one, urea, and the like. In some embodiments, the skin permeation enhancer is selected from isopropyl myristate, oleyl oleate, oleic acid, glycerol monooleate, other fatty acids and fatty acid esters with carbon chain lengths of $C_{12}$ to $C_{18}$, and combinations thereof. In some specific embodiments, the skin permeation enhancer is isopropyl myristate.

The skin permeation enhancer is typically included in the amount of about 1% to about 25% by weight of an adhesive layer, for example, about 2%, about 5%, about 10%, about 15%, about 20%, about 25%, or any ranges between the specified values, by weight of the adhesive layer. In some embodiments, the transdermal device can be substantially free of a transdermal enhancer. In some embodiments, the transdermal device is substantially free of a transdermal enhancer if the amount of any potential such enhancers is about 20% or less than the least amount that has been shown to enhance transdermal flux by about 50% or more.

In some embodiments, the skin permeation enhancer and its amount are chosen to provide certain improved flux characteristics. For example, in some embodiments, the present disclosure provides a transdermal delivery device comprising an adhesive layer comprising dextromethorphan dispersed in an adhesive, wherein the adhesive layer comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin. The term "otherwise equivalent transdermal delivery device without the skin permeation enhancer" should be understood as a control transdermal delivery device, wherein the content of the skin permeation enhancer in the adhesive layer is replaced with the adhesive, with all other aspects the same. For example, a transdermal delivery device includes an adhesive layer comprising 10% by weight of a skin permeation enhancer and 10% by weight dextromethorphan dispersed in 80% by weight acrylate adhesive, the otherwise equivalent device would include a respective adhesive layer with 10% by weight dextromethorphan dispersed in 90% by weight of the same acrylate adhesive, with all other aspects of the two devices being the same.

The skin permeation enhancer and its amount can also be adjusted to achieve flux enhancement at different time points post application. For example, in some embodiments, the permeation enhancer is in an amount to provide one or more of the following: 1) a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer; 2) a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer; and 3) a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin. As detailed in the Examples, in one example, when the amount of permeation enhancer, isopropyl myristate, is increased to about 10% by weight, significant enhancement of flux was observed even at or before 4 hours post application.

The adhesive layer with a skin permeation enhancer can be included/used in any of the transdermal delivery devices herein. For example, in some embodiments, the transdermal delivery device comprising a reservoir layer described herein can have an adhesive layer with the adhesive layer with a skin permeation enhancer. Other ingredients and suitable amounts that can be optionally included in the adhesive layer include those described herein.

In some specific embodiments, the transdermal delivery device can include an adhesive layer and a reservoir layer, wherein the adhesive layer and reservoir layer can, for example, have the ingredients and amounts shown in the table below.

| | Example | Typical amount | Preferred Amount |
|---|---|---|---|
| Adhesive Layer Ingredients | | | |
| Adhesive | Duro-Tak 287-2287 | about 65% to about 85% | about 75% to about 77.5% |
| Drug | Dextromethorphan base | about 2% to about 12% | about 10% |
| Permeation enhancer | isopropyl myristate | about 6% to about 12% | about 10% |
| Others | Kollidon, e.g., Kollidon VA64 | about 1% to about 20% | about 2.5% to about 5% |
| Reservoir Layer Ingredients | | | |
| Adhesive | Duro-Tak 287-2287 | about 20% to about 70% | about 20% to about 57.5% |
| Drug | Dextromethorphan base | about 20% to about 60% | about 30% to about 50% |
| Permeation enhancer | isopropyl myristate | about 6% to about 12% | about 10% |
| Others | Kollidon, e.g., Kollidon VA64 | about 1% to about 20% | about 2.5% to about 20% |

All amounts in the table refer to the weight percentage of the respective layer (based on final formulation) with the total amount of each layer being 100%. In some embodiments, the transdermal delivery device can have an active surface area of about 60 cm² or more, e.g., about 70 cm². In some embodiments, the transdermal delivery device is configured to provide dextromethorphan about 15 mg/day to about 40 mg/day to a user, for example, about 15 mg/day, about 20 mg/day, about 25 mg/day, about 30 mg/day, about 35 mg/day, about 40 mg/day, or any ranges between the recited values. In some embodiments, the transdermal delivery device comprises about 50 mg to about 700 mg (e.g., about 50 mg, about 100 mg, about 150 mg, about 200 mg, about 300 mg, about 400 mg, about 500 mg, about 600 mg, about 700 mg, or any range between the recited values) dextromethorphan. In some embodiments, the reservoir layer can be sandwiched between two adhesive layers which can be the same or different. Typically, such transdermal delivery device also includes a backing layer and a release liner which protects the adhesive surface prior to use. Typically, these patches can be used for a dosing frequency of less than once a day, for example, once in one day, or two days or more, e.g., once a week, or 2, 3, 4, 5, or 6 times a week, such as twice a week.

In some specific embodiments, the transdermal delivery device can include an adhesive layer, which can, for example, have the ingredients and amounts shown in the table below.

Adhesive Layer Ingredients

| | Example | Typical amount | Preferred Amount |
|---|---|---|---|
| Adhesive | Duro-Tak 287-2287 | about 65% to about 85% | about 80%, or about 75% to about 77.5% |
| Drug | Dextromethorphan base | about 2% to about 12% | about 10% |
| Permeation enhancer | isopropyl myristate | about 6% to about 12% | about 10% |
| Others | Kollidon, e.g., Kollidon VA64 | 0% to about 20% | 0%, or about 2.5% to about 5% |

All amounts in the table refer to the weight percentage of the final adhesive layer with the total amount being 100%. In some embodiments, the transdermal delivery device can have an active surface area of about 10 cm$^2$ or more, e.g., about 30 cm$^2$, about 45 cm$^2$, about 60 cm$^2$, about 75 cm$^2$, about 90 cm$^2$. In some embodiments, the transdermal delivery device is configured to provide dextromethorphan about 15 mg/day to about 40 mg/day to a user, for example, about 15 mg/day, about 20 mg/day, about 25 mg/day, about 30 mg/day, about 35 mg/day, about 40 mg/day, or any ranges between the recited values. In some embodiments, the transdermal delivery device comprises about 5 mg to about 100 mg (e.g., about 15 mg, about 30 mg, about 45 mg, about 60 mg, about 90 mg, or any range between the recited values) of dextromethorphan. Typically, such transdermal delivery device also includes a backing layer and a release liner which protects the adhesive surface prior to use. Typically, these patches can be used for a dosing frequency of no less than once a day, for example, once daily, or once in 12 hours, etc.

In Vitro Flux Characteristics

In some embodiments, the transdermal delivery device herein is configured to provide certain in vitro dextromethorphan flux profile, e.g., when tested using human cadaver skin. For example, in some embodiments, any of the transdermal delivery devices herein can be configured to provide 1) a mean cumulative dextromethorphan permeated of at least about 200 ug/cm$^2$ (ug refers to micrograms) (e.g., about 200 ug/cm$^2$ to about 2000 ug/cm$^2$) at 24 hours post application; and/or 2) a mean average flux of dextromethorphan of at least about 5 ug/cm$^2$*h (e.g., about 5 ug/cm$^2$*h to about 20 ug/cm$^2$*h, about 10 ug/cm$^2$*h to about 18 ug/cm$^2$*h) from 8 hours to 24 hours post application, when tested in vitro using human cadaver skin.

In some embodiments, the transdermal delivery device can transdermally deliver to a subject in need thereof at least about 200 ug/cm$^2$ (e.g., about 200 ug/cm$^2$ to about 2000 ug/cm$^2$) per day. In some embodiments, the transdermal delivery device is configured to have a flux characteristic such that applying the transdermal delivery device to a subject in need thereof transdermally delivers dextromethorphan about 2 mg/day to about 50 mg/day to the subject. In some embodiments, the transdermal delivery device can transdermally deliver to the subject about 5 mg/day to about 50 mg/day (e.g., about 5 mg/day, about 10 mg/day, about 20 mg/day, about 30 mg/day, about 40 mg/day, about 50 mg/day, or any ranges between the recited values) to the subject for 1 day or more (e.g., 1.5 days, 2 days, 3 days, 4 days, 5 days, 6 days, 7 days, or any ranges between the recited values). The size of the transdermal delivery device is typically about 5 cm$^2$ to about 200 cm$^2$, for example, about 10 cm$^2$ to about 100 cm$^2$.

Transdermal delivery devices with the above flux characteristics can be prepared by those skilled in the art in view of the present disclosure. Preparations of a few transdermal delivery devices are also exemplified in the Examples section. The cumulative drug (dextromethorphan, deuterated dextromethorphan, or a combination thereof) permeated can be adjusted, for example, by varying the composition of the adhesive layer (e.g., drug concentration, permeation enhancer, drug load, types of adhesives etc.).

It should be noted that the pharmaceutical composition formulated for the adhesive layer and/or the reservoir layer described herein is also a novel aspect of the present disclosure.

The transdermal delivery device herein can also be characterized by certain in vivo release profile, e.g., to provide a desired pharmacokinetic (PK) profile, e.g., any of those described herein. In some embodiments, the transdermal delivery device can be configured to provide a PK profile in a subject in need thereof, e.g., any of the PK profile described herein. In some embodiments, the transdermal delivery device is configured to provide a PK profile effective, for example, for treating a disease or disorder (e.g., described herein, such as PBA) in the subject.

TDD with Two Different Zones

In some embodiments, the transdermal delivery device can include two different zones with different release rates.

Illustrated in FIG. 7 is a view of a matrix transdermal device 100. The center matrix 20 can be for example configured (drug amount and adhesive or adhesive mixture selected) to provide more rapid onset. In the illustrative example, the added amount of pharmaceutical active in the center matrix 20 can reduce adhesion. Nonetheless, adhesion from the surrounding matrix 30 holds the device in place. Surrounding matrix 30 can be configured for example to provide longer term delivery of pharmaceutical active.

In embodiments with two different zones, the rapidly releasing portion of the device, can be for example about 5 cm$^2$ to about 150 cm$^2$, e.g., about 5 cm$^2$ to about 100 cm$^2$, or about 5 cm$^2$ to about 40 cm$^2$, etc. in area. A slower release portion can be for example about 5 cm$^2$ to about 150 cm$^2$, e.g., about 5 cm$^2$ to about 100 cm$^2$, or about 7.5 cm$^2$ to about 55 cm$^2$ in area.

Methods of Administering Dextromethorphan and PK Profiles

In various embodiments, the present invention provides a method of using the transdermal delivery device or pharmaceutical compositions described herein, for example, for administering dextromethorphan to a subject in need thereof, e.g., those suffering from any of the diseases or disorders described herein.

Some embodiments are directed to a method of administering dextromethorphan to a subject (e.g., human subject) in need thereof. In some embodiments, the subject is sensitive to or otherwise intolerant to quinidine, e.g., with QTc prolongation. In some embodiments, the method comprises applying any of the transdermal delivery devices or pharmaceutical compositions to the subject, for example, to the skin of the subject. In some embodiments, the subject is not administered dextromethorphan through another source, for example, through oral administration. However, in some embodiments, the subject can also be supplemented with another source of dextromethorphan, for example, by co-administering an oral formulation of dextromethorphan to the subject. In some embodiments, the user is characterized as an extensive metabolizer. In some embodiments, the user is characterized as a poor metabolizer. In some embodiments, the user is not co-administered a CYP2D6 inhibitor. In some embodiments, the user is not co-administered quinidine. In some embodiments, the user is co-administered a CYP2D6 inhibitor such as quinidine, bupropion, etc.

Various dosing regimen are suitable for the methods herein. For example, in some embodiments, the method comprises administering a transdermal delivery device (e.g., described herein) to the subject once daily for a desired period of time. In some embodiments, the transdermal delivery device comprises about 5 mg to about 100 mg of dextromethorphan. In some embodiments, the method can also comprise administering a transdermal delivery device (e.g., described herein) to the subject once in two days or more (e.g., once in two days, once in three days, once in four days, once in five days, once in six days, once in a week, etc.) for a desired period of time. In some embodiments, the method can also comprise administering a transdermal delivery device (e.g., described herein) to the subject once in at least one day, for example, once in two days or more (e.g., once a week), or 1, 2, 3, 4, 5, or 6 times a week for a desired period of time. In some embodiments, the method can also comprise administering a transdermal delivery device (e.g., described herein) to the subject once a week. In some embodiments, the transdermal delivery device comprises about 50 mg to about 700 mg of dextromethorphan. While the methods herein typically apply the transdermal delivery device to the subject in a frequency of once a day or once in more than 1 day, in some embodiments, the methods can also apply the transdermal delivery device to the subject in a frequency of once in less than 1 day, such as twice a day or three times a day.

The methods of administering dextromethorphan herein typically provide certain pharmacokinetic profile in a subject (e.g., human subject) in need thereof that is suitable (e.g., effective), for example, for treating a disease or disorder (e.g., any of those described herein such as PBA) in the subject.

In some embodiments, the methods comprise administering the transdermal delivery device herein to the subject to achieve an average blood $C_{max}$ of dextromethorphan of about 6 ng/mL to about 21 ng/mL (e.g., about 8 ng/mL to about 17 ng/mL or about 10 ng/mL to about 15 ng/mL) and that for a period of twelve hours or more, the A.U.C. of dextromethorphan is about the equivalent (normalized to the measuring period) of the 12 hour value of about 52 ng·h/mL to about 144 ng·h/mL (e.g., about 65 ng·h/mL to about 125 ng·h/mL, or about 75 ng·h/mL to about 110 ng·h/mL).

As detailed in the Examples section, applying to healthy human an exemplary patch containing about 35 mg dextromethorphan with a size of 45 cm², which was designed to transdermally deliver 15 mg per day and contains, in the adhesive layer (drug-in-adhesive layer) about 80% by weight of an adhesive (Duro-Tak 87-2287), about 10% by weight of dextromethorphan base and about 10% by weight of permeation enhancer isopropyl myristate, for about 24 hours, achieved, inter alia, a mean $C_{max}$ of about 6 ng/mL and a mean $AUC_{0-24h}$ of about 92 h-ng/mL, which are approaching those observed from orally administering a combination of 20 mg dextromethorphan and 10 mg quinidine twice a day to the human subject. This shows for the first time that transdermal delivery of dextromethorphan, without using quinidine, can provide a significant blood level of dextromethorphan in human. Further, the human PK data allows a skilled person to adjust the patch design to achieve a desired PK profile.

For example, in some embodiments, the method comprises, consists essentially of, or consists of, applying a transdermal delivery device (e.g., described herein) comprising dextromethorphan to the skin of the subject (e.g., human subject) once daily (e.g., for up to 7 days or more or for at least 7 days or any desired period of time), wherein the applying results in one or more (1, 2, 3, 4, 5, 6, 7, 8, or all), in any combinations, of the following pharmacokinetic profile in the subject: 1) a mean $C_{max}$ of dextromethorphan of at least about 3 ng/ml (e.g., about 3 ng/ml to about 12 ng/ml) at day 1 post application (i.e., measured for the period from time 0 to 24 hours post application); 2) a mean $AUC_{0-24}$ of dextromethorphan of at least about 40 ng*h/ml (e.g., about 40 ng*h/ml to about 150 ng*h/ml) at day 1 post application; 3) a mean ratio of $C_{24h}/C_{12h}$ of dextromethorphan of not more than about 1.5 (e.g., about 1 to about 1.5) at day 1 post application; 4) a mean ratio of $C_{24h}/C_{6h}$ of dextromethorphan of at least about 1.2 (e.g., about 1.5 to about 2.5) at day 1 post application; 5) a mean ratio of $C_{24h}/C_{18h}$ of dextromethorphan of about 0.85 to about 1.3 at day 1 post application; 6) a mean $C_{max}$ of dextrorphan of not more than 2 ng/ml (e.g., not more than 2 ng/ml, not more than 1 ng/ml, or not more than 0.5 ng/ml) at day 1 post application; 7) a mean $AUC_{0-24}$ of dextrorphan of not more than 10 ng*h/ml (e.g., not more than 10 ng*h/ml or not more than 5 ng*h/ml) at day 1 post application; 8) a mean ratio of $C_{max}$ of dextromethorphan to $C_m$ of dextrophan of at least about 5 (e.g., at least about 10, at least about 15, at least about 20) at day 1 post application; and 9) a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application. In some embodiments, the applying results in a PK profile in the subject comprising: a). 1) and/or 2); b). 3), 4), and/or 5); c). 6) and/or 7); d). 8) and/or 9); or e). any combination of a), b), c), and d).

In some embodiments, the method can comprise, consist essentially of, or consist of, applying a transdermal delivery device (e.g., described herein) comprising dextromethorphan to the skin of the subject (e.g., human subject) once in at least one day (e.g., once in two days or more (e.g., once in two days, once in three days, once in four days, once in five days, once in six days, once in a week, etc.) (e.g., for up to 7 days or more or for at least 7 days or any desired period of time), wherein the applying results in one or more (1, 2, 3, 4, 5, 6, 7, 8, or all), in any combinations, of the following pharmacokinetic profile in the subject: 1) a mean $C_{max}$ of dextromethorphan of at least about 3 ng/ml (e.g., about 3 ng/ml to about 12 ng/ml) at day 1 post application; 2) a mean $AUC_{0-24}$ of dextromethorphan of at least about 40 ng*h/ml (e.g., about 40 ng*h/ml to about 150 ng*h/ml) at day 1 post application; 3) a mean ratio of $C_{24h}/C_{12h}$ of dextromethorphan of not more than about 1.5 (e.g., about 1 to about 1.5) at day 1 post application; 4) a mean ratio of $C_{24h}/C_{6h}$ of dextromethorphan of at least about 1.2 (e.g., about 1.5 to about 2.5) at day 1 post application; 5) a mean ratio of $C_{24h}/C_{18h}$ of dextromethorphan of about 0.85 to about 1.3 at day 1 post application; 6) a mean $C_{max}$ of dextrorphan of not more than 2 ng/ml (e.g., not more than 2 ng/ml, not more than 1 ng/ml, or not more than 0.5 ng/ml) at day 1 post application; 7) a mean $AUC_{0-24}$ of dextrorphan of not more than 10 ng*h/ml (e.g., not more than 10 ng*h/ml or not more than 5 ng*h/ml) at day 1 post application; 8) a mean ratio of $C_{max}$ of dextromethorphan to $C_{max}$ of dextrophan of at least about 5 (e.g., at least about 10, at least about 15, at least about 20) at day 1 post application; and 9) a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application. In some embodiments, the applying results in a PK profile in the subject comprising: a). 1) and/or 2); b). 3), 4), and/or 5); c). 6) and/or 7); d). 8) and/or 9); or e). any combination of a), b), c), and d). In some embodiments, the method with a once at least 1 day application results in substantially the same PK profile for day 1 post application as that observed with the once daily method described herein.

The plasma concentration from the transdermal delivery device herein can be maintained substantially constant and the peak to trough ratio is typically lower than those observed from orally administering Neudexta twice a day. For example, in some embodiments, the method comprises applying the transdermal delivery device to the skin of the subject (e.g., human subject) once a week, wherein the applying results in i) a mean ratio of $C_{24h}/C_{12h}$ of dextromethorphan of not more than 2 (e.g., about 0.85 to about 1.3) at day 7 post application; ii) a mean ratio of $C_{24h}/C_{6h}$ of dextromethorphan of not more than 2 (e.g., about 0.85 to about 1.3) at day 7 post application; and/or iii) a mean ratio of $C_{24h}/C_{18h}$ of dextromethorphan of not more than 2 (e.g., about 0.85 to about 1.3) at day 7 post application. In some embodiments, the applying results in at least two of i)-iii). In some embodiments, the applying results in all of i)-iii). The once daily methods described herein can also result in a relatively low peak to trough ratio, which is typically lower than the corresponding ratio observed from orally administering Neudexta twice a day, for example, when measured for a time period after steady state is reached.

In some embodiments, the methods herein can be adjusted to achieve a $C_{max}$ and/or AUC of dextromethorphan according to different needs, for example, to match (or approach) those observed for orally administering a combination of 20 mg dextromethorphan and 10 mg quinidine twice a day.

For example, in some embodiments, the method comprises applying the transdermal delivery device herein to the subject (e.g., human subject) once daily or once a week, for up to 7 days or more or for at least 7 days or any desired period of time, wherein the applying results in i) a mean $C_{max}$ of dextromethorphan of at least about 8 ng/ml (e.g., about 8 ng/ml to about 20 ng/ml) at day 7 post application; and/or ii) a mean $C_{max}$ of dextrorphan of not more than 2 ng/ml (e.g., e.g., not more than 2 ng/ml, not more than 1 ng/ml, or not more than 0.5 ng/ml) at day 7 post application. In some embodiments, the applying results in one or more of the following PK profile: a) a mean $C_{max}$ of dextromethorphan of at least about 30% (e.g., about 30% to about 80%) of that observed from orally administering a combination of 20 mg dextromethorphan and 10 mg quinidine twice a day to the subject (e.g., human subject) for 7 days; b) a mean $AUC_{0-24}$ of dextromethorphan of at least about 30% (e.g., about 30% to about 80%) of that observed from orally administering a combination of 20 mg dextromethorphan and 10 mg quinidine twice a day to the subject (e.g., human subject) for 7 days; c) a mean $C_m$ of dextrorphan of not more than about 50% (e.g., about 10% to about 30%) of that observed from orally administering a combination of 20 mg dextromethorphan and 10 mg quinidine twice a day to the subject (e.g., human subject) for 7 days; and d) a mean $AUC_{0-24}$ of dextrorphan of not more than about 50% (e.g., about 10% to about 30%) of that observed from orally administering a combination of 20 mg dextromethorphan and 10 mg quinidine twice a day to the subject (e.g., human subject) for 7 days, when measured at day 7 post application.

The methods herein are not limited to a particular subject or a particular class of subjects. In some embodiments, the subject is characterized as an extensive metabolizer. In some embodiments, the subject is characterized as a poor metabolizer. In some embodiments, the subject is not co-administered a CYP2D6 inhibitor. In some embodiments, the subject is not co-administered quinidine. In some embodiments, the subject is co-administered a CYP2D6 inhibitor such as quinidine, bupropion, etc. However, in any of the embodiments described herein, the subject does not suffer from a cough and/or does not need an antitussive.

In some embodiments, the subject (e.g., human subject) is characterized as having a neurological disease or disorder. In some embodiments, the subject (e.g., human subject) is characterized as having one or more diseases or disorders selected from affective disorders, psychiatric disorders, cerebral function disorders, movement disorders, dementias, motor neuron diseases, neurodegenerative diseases, seizure disorders, and headaches. In some embodiments, the subject suffers from one or more diseases or disorders selected from depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability. In some embodiments, the subject suffers from one or more diseases or disorders selected from Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia. In any of the embodiments herein, the subject can suffer from pseudobulbar affect, depression, stroke, traumatic brain injury, seizure, pain (e.g., post-operative pain, neuropathic pain), methotrexate neurotoxicity, Parkinson's disease, autism, or combinations thereof. In any of the embodiments herein, the subject can suffer from pseudobulbar affect.

Methods of Treatment

Dextromethorphan are known to be useful for treating a variety of diseases or disorders. See e.g., Nguyen, L. et al., *Pharmacology* & *Therapeutics* 159:1022 (2016). Thus, in some embodiments, the present disclosure is also directed to a method of treating a disease or disorder in a subject in need thereof. In some embodiments, the method comprises transdermally administering to the subject a therapeutically effective amount of dextromethorphan. In some embodiments, the administering comprises applying the transdermal delivery device to the skin of the subject. In some embodiments, the administering results in a PK profile described herein. In some embodiments, the subject does not suffer from a cough and/or does not need an antitussive agent. In some embodiments, the subject is an extensive metabolizer of dextromethorphan. In some embodiments, the subject is a poor metabolizer of dextromethorphan. In some embodiments, the subject is sensitive to or otherwise intolerant to quinidine, e.g., with QTc prolongation.

Various diseases and disorders are suitable to be treated by the methods herein. In some embodiments, the disease or disorder is a neurological disorder. Non-limiting exemplary neurological diseases or disorders include affective disorders, psychiatric disorders, cerebral function disorders, movement disorders, dementias, motor neuron diseases, neurodegenerative diseases, seizure disorders, and headaches.

Affective disorders that can be treated by methods herein include, but are not limited to, depression, major depression, treatment resistant depression and treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Psychiatric disorders that can be treated by the methods herein include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease.

Substance addiction abuse that can be treated by the methods herein include, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that can be treated by the methods herein include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Movement disorders that can be treated by the methods herein include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that can be treated by the methods herein include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that can be treated by the methods herein include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that can be treated by the methods herein include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that can be treated by the methods herein include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that can be treated by the methods herein include, but are not limited to, migraine, tension, and cluster headaches.

Other neurological disorders that can be treated by the methods herein include, but are not limited to, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the disease or disorder is pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

The methods herein can also be used to treat, or provide relief to, any type of pain including, but not limited to, musculoskeletal pain, neuropathic pain, cancer-related pain, acute pain, nociceptive pain, inflammatory pain, arthritis pain, complex regional pain syndrome, etc.

In some embodiments, the disease or disorder can be allodynia, treatment refractory hyperalgesia, dermatitis, pain, inflammation or inflammatory conditions, such as Crohn's disease, including pain associated with inflammation, psoriasis, cancer, viral infection, or as an adjuvant treatment for multiple myeloma.

In any of the embodiments described herein, the method can be for treating pseudobulbar affection, depression, stroke, traumatic brain injury, seizure, pain (e.g., postoperative pain, neuropathic pain), methotrexate neurotoxicity, Parkinson's disease, autism, or a combination thereof.

Suitable dosing regimen, dosing amount, duration, transdermal delivery devices, etc. include any of those described herein in any combination. In any of the embodiments described herein, the subject can be a human subject.

In some specific embodiments, the present disclosure provides a method of treating pseudobulbar affection comprising applying the transdermal delivery device herein to a subject in need thereof. In some embodiments, the transdermal delivery device comprises about 5 mg to about 100 mg of dextromethorphan. In some embodiments, the transdermal delivery device is applied once daily, e.g., for a period of time up to 7 days, at least 7 days, 1 month, or any period of time desired. In some embodiments, the transdermal delivery device comprises about 50 mg to about 700 mg of dextromethorphan. In some embodiments, the transdermal delivery device is applied once a week, e.g., for 1 week, 1 month, or any period of time desired. In some embodiments, the transdermal delivery device is applied 1, 2, 3, 4, 5, or 6 times in a week, e.g., for 1 week, 1 month, or any period of time desired. In some embodiments, the transdermal delivery device is applied to achieve any of the pharmacokinetic profile described herein. In some embodiments, the subject is not administered a CYP2D6 inhibitor. In some embodiments, the subject is not administered quinidine. In some embodiments, the subject does not suffer from a cough or need an antitussive effect. In some embodiments, the subject is characterized as a poor metabolizer. In some embodiments, the subject is characterized as an extensive metabolizer.

Combination Therapy

In some embodiments, the methods herein can further comprise administering to the subject an active agent other than dextromethorphan. For example, in some embodiments, the method described herein further comprises administering to the subject an antidepressant. In some embodiments, the antidepressant is selected from bupropion, hydroxybupropion, erythrohydroxybupropion, threohydroxybupropion, a metabolite or prodrug of any of these compounds, and combinations thereof. Other suitable antidepressants are described for example in U.S. Pat. No. 9,861,595, the content of which is incorporated by reference in its entirety. In some embodiments, the method described herein further comprises administering to the subject quinidine. In some embodiments, the method described herein further comprises administering to the subject a CYP2D6 inhibitor. In some embodiments, the method described herein further comprises administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof. These additional agents can be administered simultaneously or sequentially. Further, these additional agents can be administered via the same or a different route. For example, in some embodiments, the additional agent can be administered transdermally or orally. However, in some embodiments, the additional agent can also be combined with dextromethorphan in the same transdermal delivery device.

Because the transdermal application described herein bypasses the first-pass liver metabolism, the methods herein can provide dextromethorphan to subjects who are on medications that might interfere with liver metabolism of dextromethorphan. In some embodiments, the method comprises administering to the subject desipramine, paroxetine, thioridazine, pimozide, digoxin, atazanavir, clarithromycin, indinavir, itraconazole, ketoconazole, and combinations thereof. However, in some embodiments, the subject is not administered any of desipramine, paroxetine, thioridazine, pimozide, digoxin, atazanavir, clarithromycin, indinavir, itraconazole, ketoconazole, and combinations thereof. In some embodiments, the method does not require determining and/or is without regard to whether the subject is an extensive metabolizer or poor metabolizer of dextromethorphan.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients/materials employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the term "cumulative drug permeated" refers to the total amount of drug permeated per square centimeter during a given period of time. Unless otherwise obvious from context, "cumulative drug permeated" at a given time (e.g., at 24 hours post administration) refers to the total amount of drug permeated per square centimeter from time 0 (i.e., time of administration) to the given time. Unless otherwise obvious from context, "cumulative drug permeated" refers to the arithmetic mean value measured and/or calculated in accordance with the methods described herein. The term "mean value" as used herein, when not specified, also refers to arithmetic mean value, unless contradictory to common practice in the field.

As used herein, the term "flux" refers to the quantity of the drug permeated skin per unit area per unit time. Unless otherwise obvious from context, "flux" refers to the arithmetic mean value measured and/or calculated in accordance with the methods described herein. A typical unit of flux is milligram per square centimeter per hour.

Flux rate as referenced in this patent application can mean that measured by either in vivo or in vitro methods. One way to measure flux is to place the transdermal delivery device or formulation on a known skin area of a human volunteer and measure how much drug can permeate across skin within certain time constraints. Those skilled in the art would understand that in some cases, the absolute value of in vitro flux can be several fold different when measured using a different cadaver source. As used herein, when specifically referenced as measured by in vitro method using human cadaver skin, the flux rate should be understood as measured in accordance with the method described in Example 2. For example, a patch tested in Example 2 can be used as a reference patch, which when tested in a method in accordance with Example 2, should yield the same flux as observed in Example 2, within experimental error generally accepted by those skilled in the art. Although an in vitro method uses human epidermal membrane obtained from a cadaver, rather than measure drug flux across the skin using human volunteers, it is generally accepted by those skilled in the art that results from a properly designed and executed in vitro test can be used to estimate or predict the results of an in vivo test with reasonable reliability.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated.

The term "therapeutically effective amount," as used herein, refers to that amount of a therapeutic agent (e.g., dextromethorphan) sufficient to result in amelioration of one or more symptoms of a disorder or condition (e.g., PBA), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment.

As used herein, applying or administering the transdermal delivery device herein should be understood as in accordance with how such transdermal delivery device is normally applied or administered, e.g., to the skin of a human subject.

EXEMPLARY EMBODIMENTS

Exemplary Embodiments A1-55

1. A transdermal delivery device comprising
   a. an adhesive layer comprising an adhesive, which optionally comprises dextromethorphan dispersed in the adhesive in an amount of about 2% to about 12% by weight of the adhesive layer; and
   b. a reservoir layer comprising dextromethorphan in an amount of at least 10% (e.g., about 20% to about 60%) by weight of the reservoir layer.
2. The transdermal delivery device of embodiment A1, wherein the transdermal delivery device is configured to transdermally deliver dextromethorphan to a user about 2 mg/day to about 50 mg/day.
3. The transdermal delivery device of embodiment A1 or 2, wherein the transdermal delivery device is configured to transdermally deliver dextromethorphan to a user about 5 mg/day to about 50 mg/day (e.g., about 5 mg/day, about 10 mg/day, about 20 mg/day, about 30 mg/day, about 40 mg/day, about 50 mg/day, or any ranges between the recited values) for 1 day or more (e.g., 1.5 days, 2 days, 3 days, 4 days, 5 days, 6 days, 7 days, or any ranges between the recited values).
4. The transdermal delivery device of any one of embodiments A1-3, which has a total dextromethorphan loading of about 0.5 mg/cm² to about 8 mg/cm².
5. The transdermal delivery device of any one of embodiments A1-4, which has a total dextromethorphan loading of about 2 mg/cm² to about 6 mg/cm² (e.g., about 2 mg/cm², about 3 mg/cm², about 4 mg/cm², about 5 mg/cm², about 6 mg/cm², or any ranges between the recited values).

6. The transdermal delivery device of any one of embodiments A1-5, which has an active surface area of about 5 cm² to about 200 cm².
7. The transdermal delivery device of any one of embodiments A1-6, which has an active surface area of about 10 cm² to about 150 cm².
8. The transdermal delivery device of any one of embodiments A1-7, which has an active surface area of about 30 cm² to about 100 cm² (e.g., about 30 cm², about 40 cm², about 50 cm², about 60 cm², about 70 cm², about 80 cm², about 90 cm², about 100 cm², or any ranges between the recited values).
9. The transdermal delivery device of any one of embodiments A1-8, wherein the adhesive layer comprises dextromethorphan in an amount of about 6% to about 12% (e.g., about 6%, about 7%, about 8%, about 9%, about 10%, about 11%, about 12%, or any ranges between the recited values) by weight of the adhesive layer.
10. The transdermal delivery device of any one of embodiments A1-9, wherein the adhesive layer further comprises a skin permeation enhancer.
11. The transdermal delivery device of embodiment A10, wherein the skin permeation enhancer is selected from isopropyl myristate, oleyl oleate, oleic acid, glycerol monooleate, other fatty acids and fatty acid esters with carbon chain lengths of $C_{12}$ to $C_{18}$, and combinations thereof.
12. The transdermal delivery device of embodiment A10 or 11, wherein the skin permeation enhancer is present in an amount of about 2% to about 15% by weight of the adhesive layer.
13. The transdermal delivery device of any one of embodiments A10-12, wherein the skin permeation enhancer is present in an amount of about 6% to about 12% (e.g., about 6%, about 7%, about 8%, about 9%, about 10%, about 11%, about 12%, or any ranges between the recited values) by weight of the adhesive layer.
14. The transdermal delivery device of any one of embodiments A1-13, wherein the adhesive layer further comprises an agent to improve cohesive strength of the adhesive layer.
15. The transdermal delivery device of any one of embodiments A1-13, wherein the adhesive layer further comprises an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof.
16. The transdermal delivery device of embodiment A14 or 15, wherein the agent is present in an amount of about 1% to about 20% by weight of the adhesive layer.
17. The transdermal delivery device of any one of embodiments A14-16, wherein the agent is present in an amount of about 2% to about 20% (e.g., about 2%, about 2.5%, about 3%, about 4%, about 5%, about 6%, about 10%, about 15%, about 20%, or any ranges between the recited values), for example, about 2% to about 6% (e.g., about 2%, about 2.5%, about 3%, about 4%, about 5%, or any ranges between the recited values) by weight of the adhesive layer.
18. The transdermal delivery device of any one of embodiments A1-17, wherein the adhesive comprises a pressure sensitive adhesive.
19. The transdermal delivery device of embodiment A18, wherein the pressure sensitive adhesive comprises a polyisobutylene adhesive, a silicone polymer adhesive, an acrylate copolymer adhesive (e.g., a poly acrylate vinyl acetate copolymer, such as Duro-Tak 87-2287), or a combination thereof.

20. The transdermal delivery device of embodiment A18 or 19, wherein the pressure sensitive adhesive is present in an amount of about 50% to about 90% by weight of the adhesive layer.

21. The transdermal delivery device of any one of embodiments A18-20, wherein the pressure sensitive adhesive is present in an amount of about 60% to about 85% (e.g., about 60%, about 70%, about 75%, about 80%, about 85%, or any ranges between the recited values) by weight of the adhesive layer.

22. The transdermal delivery device of any one of embodiments A1-21, wherein the adhesive layer is capable of adhering to a user's skin continuously for at least 1 day (e.g., at least 2 days, at least 3 days, at least 4 days, at least 5 days, at least 6 days, at least 7 days).

23. The transdermal delivery device of any one of embodiments A1-22, wherein the adhesive layer is about 0.1 mil to about 10 mils thick (e.g., about 0.5 mil to about 10 mils, about 1 mil to 10 mils).

24. The transdermal delivery device of any one of embodiments A1-23, wherein the reservoir layer comprises dextromethorphan in an amount of about 30% to about 50% (e.g., about 30%, about 35%, about 40%, about 45%, about 50%, or any ranges between the recited values) by weight of the reservoir layer.

25. The transdermal delivery device of any one of embodiments A1-24, wherein the reservoir layer further comprises a skin permeation enhancer.

26. The transdermal delivery device of embodiment A25, wherein the skin permeation enhancer is selected from isopropyl myristate, oleyl oleate, oleic acid, glycerol monooleate, other fatty acids and fatty acid esters with carbon chain lengths of $C_{12}$ to $C_{18}$, and combinations thereof.

27. The transdermal delivery device of embodiment A25 or 26, wherein the skin permeation enhancer is present in an amount of about 2% to about 15% by weight of the reservoir layer.

28. The transdermal delivery device of any one of embodiments A25-27, wherein the skin permeation enhancer is present in an amount of about 6% to about 12% (e.g., about 6%, about 7%, about 8%, about 9%, about 10%, about 11%, about 12%, or any ranges between the recited values) by weight of the reservoir layer.

29. The transdermal delivery device of any one of embodiments A1-28, wherein the reservoir layer further comprises an agent to improve cohesive strength of the reservoir layer.

30. The transdermal delivery device of any one of embodiments A1-28, wherein the reservoir layer further comprises an agent selected from a vinylpyrrolidone polymer (e.g., a vinylpyrrolidone-vinyl acetate copolymers), Kollidon (e.g., Kollidon 30 LP, Kollidon 90, or Kollidon VA64), silicone dioxide, titanium dioxide, and combinations thereof.

31. The transdermal delivery device of embodiment A29 or 30, wherein the agent is present in an amount of about 1% to about 20% by weight of the reservoir layer.

32. The transdermal delivery device of any one of embodiments A29-31, wherein the agent is present in an amount of about 2% to about 20% (e.g., about 2%, about 2.5%, about 3%, about 4%, about 5%, about 6%, about 10%, about 15%, about 20%, or any ranges between the recited values), for example, about 2% to about 6% (e.g., about 2%, about 2.5%, about 3%, about 4%, about 5%, or any ranges between the recited values) by weight of the reservoir layer.

33. The transdermal delivery device of any one of embodiments A1-32, wherein the reservoir layer comprises dextromethorphan dispersed, e.g., homogenously dispersed, in a pressure sensitive adhesive.

34. The transdermal delivery device of embodiment A33, wherein the pressure sensitive adhesive comprises a polyisobutylene adhesive, a silicone polymer adhesive, an acrylate copolymer adhesive (e.g., a poly acrylate vinyl acetate copolymer, such as Duro-Tak 87-2287), or a combination thereof.

35. The transdermal delivery device of embodiment A33 or 34, wherein the pressure sensitive adhesive is present in an amount of about 20% to about 80% by weight of the reservoir layer.

36. The transdermal delivery device of any one of embodiments A33-35, wherein the pressure sensitive adhesive is present in an amount of about 20% to about 65% (e.g., about 20%, about 30%, about 35%, about 40%, about 50%, about 60%, about 65%, or any ranges between the recited values) by weight of the reservoir layer.

37. The transdermal delivery device of any one of embodiments A1-36, wherein the reservoir layer is about 0.1 mil to about 10 mils thick (e.g., about 0.5 mil to about 10 mils, about 1 mil to about 10 mils).

38. The transdermal delivery device of any one of embodiments A1-37, wherein the adhesive layer and reservoir layer are separated by a rate-controlling membrane.

39. A method of administering dextromethorphan to a subject in need thereof, the method comprising applying the transdermal delivery device of any one of embodiments A1-38 or C1-21 to the subject, or the method comprising applying to the subject a transdermal delivery device comprising an adhesive layer having the same or substantially the same ingredients as in Formulation A, B, C1, C2, C3, D0, D1, or D2 in the Examples.

40. The method of embodiment A39, wherein the subject does not suffer from a cough and/or does not need an antitussive.

41. The method of embodiment A39 or 40, wherein the subject is characterized as an extensive metabolizer.

42. The method of any one of embodiments A39-41, wherein the subject suffers from a neurological disease or disorder.

43. The method of any one of embodiments A39-41, wherein the subject suffers from one or more diseases or disorders selected from affective disorders, psychiatric disorders, cerebral function disorders, movement disorders, dementias, motor neuron diseases, neurodegenerative diseases, seizure disorders, and headaches.

44. The method of any one of embodiments A39-41, wherein the subject suffers from one or more diseases or disorders selected from depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

45. The method of any one of embodiments A39-41, wherein the subject suffers from one or more diseases or disorders selected from Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

46. The method of any one of embodiments A39-41, wherein the subject suffers from pseudobulbar affect, depression, stroke, traumatic brain injury, seizure, pain (e.g., post-operative pain, neuropathic pain), methotrexate neurotoxicity, Parkinson's disease, autism, or combinations thereof.

47. The method of any one of embodiments A39-46, further comprising administering to the subject an antidepressant.

48. The method of embodiment A47, wherein the antidepressant is selected from bupropion, hydroxybupropion, erythrohydroxybupropion, threohydroxybupropion, a metabolite or prodrug of any of these compounds, and combinations thereof.

49. The method of any one of embodiments A39-46, further comprising administering to the subject quinidine.

50. The method of any one of embodiments A39-46, wherein the subject is not administered a CYP2D6 inhibitor.

51. The method of any one of embodiments A39-46, wherein the subject is not administered quinidine.

52. The method of any one of embodiments A39-46, wherein the subject is not administered any of desipramine, paroxetine, thioridazine, pimozide, digoxin, atazanavir, clarithromycin, indinavir, itraconazole, ketoconazole, and combinations thereof.

53. The method of any one of embodiments A39-46, further comprising administering to the subject one or more additional active agents selected from amlodipine, a capsaicinoid (e.g., capsaicin or an ester thereof), an opioid agonist (e.g., a μ-opiate analgesic (e.g., tramadol)), an adenosinergic agonist, 3-(3-dimethylamino-1-ethyl-2-methyl-propyl)-phenol, gabapentin, and pharmaceutically acceptable salts thereof.

54. The method of any one of embodiments A39-53, wherein the transdermal delivery device is applied once daily, e.g., for a period of up to 7 days or more, or for at least 7 days or any desired period of time.

55. The method of any one of embodiments A39-53, wherein the transdermal delivery device is applied once a week or 2, 3, 4, 5, or 6 times a week.

Exemplary Embodiments B1-26

1. A method of administering dextromethorphan to a human subject in need thereof, the method comprising applying a transdermal delivery device comprising dextromethorphan to the skin of the subject once daily, wherein the applying results in one or more of the following pharmacokinetic profile in the human subject:

a. a mean $C_{max}$ of dextromethorphan of at least about 3 ng/ml (e.g., about 3 ng/ml to about 12 ng/ml) at day 1 post application;

b. a mean $AUC_{0-24}$ of dextromethorphan of at least about 40 ng*h/ml (e.g., about 40 ng*h/ml to about 150 ng*h/ml) at day 1 post application;

c. a mean ratio of $C_{24h}/C_{12h}$ of dextromethorphan of not more than about 1.5 (e.g., about 1 to about 1.5) at day 1 post application;

d. a mean ratio of $C_{24h}/C_{6h}$ of dextromethorphan of at least about 1.2 (e.g., about 1.5 to about 2.5) at day 1 post application;

e. a mean ratio of $C_{24h}/C_{18h}$ of dextromethorphan of about 0.85 to about 1.3 at day 1 post application;

f. a mean $C_{max}$ of dextrorphan of not more than 2 ng/ml (e.g., not more than 2 ng/ml, not more than 1 ng/ml, or not more than 0.5 ng/ml) at day 1 post application;

g. a mean $AUC_{0-24}$ of dextrorphan of not more than 10 ng*h/ml (e.g., not more than 10 ng*h/ml or not more than 5 ng*h/ml) at day 1 post application;

h. a mean ratio of $C_{max}$ of dextromethorphan to $C_{max}$ of dextrophan of at least about 5 (e.g., at least about 10, at least about 15, at least about 20) at day 1 post application; and i. a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application.

2. The method of embodiment B1, wherein the human subject does not suffer from a cough and/or does not need an antitussive.

3. The method of embodiment B1 or 2, wherein the human subject is characterized as an extensive metabolizer.

4. The method of any one of embodiments B1-3, wherein the applying results in a mean $C_{max}$ of dextromethorphan of at least about 30% (e.g., about 30% to about 80%) of that observed from orally administering a combination of 20 mg dextromethorphan and 10 mg quinidine twice a day to the human subject, when measured at day 1 post application.

5. The method of any one of embodiments B1-4, wherein the applying results in a mean $AUC_{0-24}$ of dextromethorphan of at least about 30% (e.g., about 30% to about 80%) of that observed from orally administering a combination of 20 mg dextromethorphan and 10 mg quinidine twice a day to the human subject, when measured at day 1 post application.

6. The method of any one of embodiments B1-5, wherein the applying results in a mean $C_{max}$ of dextrorphan of not more than about 50% (e.g., about 10% to about 30%) of that observed from orally administering a combination of 20 mg dextromethorphan and 10 mg quinidine twice a day to the human subject, when measured at day 1 post application.

7. The method of any one of embodiments B1-6, wherein the applying results in a mean $AUC_{0-24}$ of dextrorphan of not more than about 50% (e.g., about 10% to about 30%) of that observed from orally administering a combination of 20 mg dextromethorphan and 10 mg quinidine twice a day to the human subject, when measured at day 1 post application.

8. The method of any one of embodiments B1-7, wherein the human subject suffers from pseudobulbar affection, depression, stroke, traumatic brain injury, seizure, pain (e.g., post-operative pain, neuropathic pain), methotrexate neurotoxicity, Parkinson's disease, autism, or a combination thereof.

9. The method of any one of embodiments B1-8, comprising applying the transdermal delivery device once a day for a period of time up to seven days or for at least 7 days or any desired period of time, wherein the applying results in one or both of the following pharmacokinetic profile in the human subject:
a. a mean $C_{max}$ of dextromethorphan of at least about 8 ng/ml (e.g., about 8 ng/ml to about 20 ng/ml) at day 7 post application; and
b. a mean $C_{max}$ of dextrorphan of not more than 2 ng/ml (e.g., e.g., not more than 2 ng/ml, not more than 1 ng/ml, or not more than 0.5 ng/ml) at day 7 post application.

10. The method of any one of embodiments B1-9, wherein the transdermal delivery device comprises about 5 mg to about 100 mg of dextromethorphan.

11. A method of administering dextromethorphan to a human subject in need thereof, the method comprising applying a transdermal delivery device comprising dextromethorphan to the skin of the subject once a week or 2, 3, 4, 5, or 6 times a week, wherein the applying results in one or more of the following pharmacokinetic profile in the human subject:
a. a mean $C_{max}$ of dextromethorphan of at least about 3 ng/ml (e.g., about 3 ng/ml to about 12 ng/ml) at day 1 post application;
b. a mean $AUC_{0-24}$ of dextromethorphan of at least about 40 ng*h/ml (e.g., about 40 ng*h/ml to about 150 ng*h/ml) at day 1 post application;
c. a mean ratio of $C_{24h}/C_{12h}$ of dextromethorphan of not more than about 1.5 (e.g., about 1 to about 1.5) at day 1 post application;
d. a mean ratio of $C_{24h}/C_{6h}$ of dextromethorphan of at least about 1.2 (e.g., about 1.5 to about 2.5) at day 1 post application;
e. a mean ratio of $C_{24h}/C_{18h}$ of dextromethorphan of about 0.85 to about 1.3 at day 1 post application;
f. a mean $C_{max}$ of dextrorphan of not more than 2 ng/ml (e.g., not more than 2 ng/ml, not more than 1 ng/ml, or not more than 0.5 ng/ml) at day 1 post application;
g. a mean $AUC_{0-24}$ of dextrorphan of not more than 10 ng*h/ml (e.g., not more than 10 ng*h/ml or not more than 5 ng*h/ml) at day 1 post application;
h. a mean ratio of $C_{max}$ of dextromethorphan to $C_{max}$ of dextrophan of at least about 5 (e.g., at least about 10, at least about 15, at least about 20) at day 1 post application; and
i. a mean ratio of $AUC_{0-24}$ of dextromethorphan to $AUC_{0-24}$ of dextrophan of at least about 5 (e.g., at least about 10, at least about 15, at least about 20, or at least about 25) at day 1 post application.

12. The method of embodiment B11, wherein the applying further results in one or both of the following pharmacokinetic profile in the human subject:
a. a mean $C_{max}$ of dextromethorphan of at least about 8 ng/ml (e.g., about 8 ng/ml to about 20 ng/ml) at day 7 post application; and
b. a mean $C_{max}$ of dextrorphan of not more than 2 ng/ml (e.g., e.g., not more than 2 ng/ml, not more than 1 ng/ml, or not more than 0.5 ng/ml) at day 7 post application.

13. The method of embodiment B11 or 12, wherein the human subject does not suffer from a cough and/or does not need an antitussive.

14. The method of any one of embodiments B11-13, wherein the human subject is characterized as an extensive metabolizer.

15. The method of any one of embodiments B11-14, wherein the applying results in a mean $C_{max}$ of dextromethorphan of at least about 30% (e.g., about 30% to about 80%) of that observed from orally administering a combination of 20 mg dextromethorphan and 10 mg quinidine twice a day to the human subject for 7 days, when measured at day 7 post application.

16. The method of any one of embodiments B11-15, wherein the applying results in a mean $AUC_{0-24}$ of dextromethorphan of at least about 30% (e.g., about 30% to about 80%) of that observed from orally administering a combination of 20 mg dextromethorphan and 10 mg quinidine twice a day to the human subject for 7 days, when measured at day 7 post application.

17. The method of any one of embodiments B11-16, wherein the applying results in a mean $C_{max}$ of dextrorphan of not more than about 50% (e.g., about 10% to about 30%) of that observed from orally administering a combination of 20 mg dextromethorphan and 10 mg quinidine twice a day to the human subject for 7 days, when measured at day 7 post application.

18. The method of any one of embodiments B11-17, wherein the applying results in a mean $AUC_{0-24}$ of dextrorphan of not more than about 50% (e.g., about 10% to about 30%) of that observed from orally administering a combination of 20 mg dextromethorphan and 10 mg quinidine twice a day to the human subject for 7 days, when measured at day 7 post application.

19. The method of any one of embodiments B11-18, wherein the human subject suffers from pseudobulbar affection.

20. The method of any one of embodiments B11-19, wherein the transdermal delivery device comprises about 50 mg to about 700 mg of dextromethorphan.

21. A method of treating a disease or disorder in a subject in need thereof, the method comprising administering a transdermal delivery device comprising dextromethorphan to the skin of the subject once daily, wherein the applying results in one or more of the pharmacokinetic profile recited in embodiments B1, B3-7 and B9, wherein the disease or disorder is any of those described herein.

22. The method of embodiment 21, wherein the disease or disorder is a neurological disease or disorder, e.g., pseudobulbar affection.

23. A method of treating a disease or disorder in a subject in need thereof, the method comprising administering a transdermal delivery device comprising dextromethorphan to the skin of the subject once a week or 2, 3, 4, 5, or 6 times a week, wherein the applying results in one or more of the pharmacokinetic profile recited in embodiments B11-12 and B15-18, wherein the disease or disorder is any of those described herein.

24. The method of embodiment 21, wherein the disease or disorder is a neurological disease or disorder, e.g., pseudobulbar affection.

25. The method of any one of embodiments B1-24, wherein the transdermal delivery device is selected from the transdermal delivery device of any of embodiments A1-38 and C1-21.

26. The method of any one of embodiments B1-24, wherein the transdermal delivery device comprises an adhesive layer having the same or substantially the same ingredients as in Formulation A, B, C1, C2, C3, D0, D1, or D2 in the Examples.

Exemplary Embodiments C1-32

1. A transdermal delivery device comprising:
   an adhesive layer comprising dextromethorphan dispersed in an adhesive comprising
   an acrylate adhesive and a silicone adhesive,
   wherein the weight ratio of the acrylate adhesive to silicon adhesive ranges from about 20:1 to about 1:20.

2. The transdermal delivery device of embodiment C1, wherein the weight ratio of the acrylate adhesive to silicon adhesive ranges from about 10:1 to about 1:10 (e.g., about 10:1, about 4:1, about 1:1, about 1:4, or any ranges between the recited value).

3. The transdermal delivery device of embodiment C1 or 2, which is configured to provide a mean cumulative dextromethorphan permeated of at least about 200 ug/cm$^2$ (e.g., about 200 ug/cm$^2$ to about 2000 ug/cm$^2$) at 24 hours post application, when tested in vitro using human cadaver skin.

4. The transdermal delivery device of any one of embodiments C1-3, which is configured to provide a mean average flux of dextromethorphan of at least about 5 ug/cm$^2$*h (e.g., about 5 ug/cm$^2$*h to about 20 ug/cm$^2$*h, about 10 ug/cm$^2$*h to about 18 ug/cm$^2$*h) from 8 hours to 24 hours post application, when tested in vitro using human cadaver skin.

5. The transdermal delivery device of any one of embodiments C1-4, wherein the adhesive layer further comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

6. The transdermal delivery device of any one of embodiments C1-5, wherein the adhesive layer comprises a skin permeation enhancer in an amount to provide a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

7. The transdermal delivery device of any one of embodiments C1-6, wherein the adhesive layer comprises a skin permeation enhancer in an amount to provide a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer, when tested in vitro using human cadaver skin.

8. The transdermal delivery device of any one of embodiments C1-7, wherein the adhesive layer comprises a skin permeation enhancer in an amount to provide a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin.

9. The transdermal delivery device of any one of embodiments C1-8, which is suitable for 1-day, 2-day, 3-day, 4-day, 5-day, 6-day, or 7-day application.

10. The transdermal delivery device of embodiment C9, which is configured to provide dextromethorphan to a user of at least about 200 ug/cm$^2$ (e.g., about 200 ug/cm$^2$ to about 2000 ug/cm$^2$) per day.

11. The transdermal delivery device of any one of embodiments C1-10, which has a size of about 5 cm$^2$ to about 200 cm$^2$.

12. The transdermal delivery device of any one of embodiments C1-11, which has a size of about 10 cm$^2$ to about 100 cm$^2$.

13. A transdermal delivery device comprising:
    an adhesive layer comprising dextromethorphan dispersed in an adhesive,
    wherein the adhesive layer comprises a skin permeation enhancer in an amount to provide a mean cumulative dextromethorphan permeated at 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

14. The transdermal delivery device of embodiment C13, wherein the skin permeation enhancer is in an amount to provide a mean average flux of dextromethorphan from 8 hours to 24 hours post application of at least about 25% (e.g., about 25%, about 50%, about 100%, about 150%, about 200%, or any ranges between the recited value) higher than that of an otherwise equivalent transdermal delivery device without the skin permeation enhancer, when tested in vitro using human cadaver skin.

15. The transdermal delivery device of embodiment C13 or 14, wherein the skin permeation enhancer is in an amount to provide a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that of an otherwise equivalent transdermal delivery device without the skin permeation enhancer, when tested in vitro using human cadaver skin.

16. The transdermal delivery device of any one of embodiments C13-15, wherein the skin permeation enhancer is in an amount to provide a mean average flux of dextromethorphan from 0 hours to 4 hours post application of at least about 5-fold (e.g., about 5-fold, about 8-fold, about 10-fold, about 20-fold, or any ranges between the recited value) of that of an otherwise equivalent transdermal delivery device without the skin permeation enhancer, when tested in vitro using human cadaver skin.

17. The transdermal delivery device of any one of embodiments C13-16, which is suitable for 1-day, 2-day, 3-day, 4-day, 5-day, 6-day, or 7-day application.

18. The transdermal delivery device of embodiment C17, which is configured to provide dextromethorphan to a user of at least about 200 ug/cm$^2$ (e.g., about 200 ug/cm$^2$ to about 2000 ug/cm$^2$) per day.

19. The transdermal delivery device of any one of embodiments C13-18, which has a size of about 5 cm$^2$ to about 200 cm$^2$.

20. The transdermal delivery device of any one of embodiments C13-19, which has a size of about 10 cm$^2$ to about 100 cm$^2$.

21. The transdermal delivery device of any one of embodiments C13-20, wherein the skin permeation enhancer is selected from isopropyl myristate, oleyl oleate, oleic acid, glycerol monooleate, other fatty acids and fatty acid esters with carbon chain lengths of C$_{12}$ to C$_{18}$, and combinations thereof.

22. A method of administering dextromethorphan to a subject in need thereof, the method comprising applying a transdermal delivery device to the skin of the subject, wherein the transdermal delivery device comprises an adhesive layer, wherein the adhesive layer comprises dextromethorphan dispersed in an adhesive, and a skin permeation enhancer, wherein the skin permeation enhancer is in an amount such that the applying results in a mean cumulative dextromethorphan permeated at 24 hours post application of at least about 25% (e.g., about 25%, about 50%, about 100%, about 150%, about 200%, or any ranges between the recited value) higher than that from applying an otherwise equivalent transdermal delivery device without the skin permeation enhancer.

23. The method of embodiment C22, wherein the skin permeation enhancer is in an amount such that the applying results in a mean average flux of dextromethorphan from 8 hours to 24 hours post application of at least about 25% (e.g., about 25%, about 50%, about 100%, about 150%, about 200%, or any ranges between the recited value) higher than that from applying an otherwise equivalent transdermal delivery device without the skin permeation enhancer.

24. The method of embodiment C22 or 23, wherein the skin permeation enhancer is in an amount such that the applying results in a mean average flux of dextromethorphan from 4 hours to 8 hours post application of at least about 2-fold (e.g., about 3-fold, about 4-fold, about 5-fold, about 8-fold, about 10-fold, or any ranges between the recited value) of that from applying an otherwise equivalent transdermal delivery device without the skin permeation enhancer.

25. The method of any one of embodiments C22-24, wherein the skin permeation enhancer is in an amount such that the applying results in a mean average flux of dextromethorphan from 0 hours to 4 hours post application of at least about 5-fold (e.g., about 5-fold, about 8-fold, about 10-fold, about 20-fold, or any ranges between the recited value) of that from applying an otherwise equivalent transdermal delivery device without the skin permeation enhancer.

26. The method of any one of embodiments C22-25, wherein the transdermal delivery device is applied once a day for 1 day or more, (e.g., 1 day, 2 days, 3 days, 4 days, 5 days, 6 days, or 7 days, or more).

27. The method of embodiment C26, which transdermally delivers dextromethorphan to the subject at least about 200 ug/cm$^2$ (e.g., about 200 ug/cm$^2$ to about 2000 ug/cm$^2$) per day.

28. The method of any one of embodiments C22-27, wherein the transdermal delivery device has a size of about 5 cm$^2$ to about 200 cm$^2$.

29. The method of any one of embodiments C22-28, wherein the transdermal delivery device has a size of about 10 cm$^2$ to about 100 cm$^2$.

30. The method of any one of embodiments C22-29, wherein the skin permeation enhancer is selected from isopropyl myristate, oleyl oleate, oleic acid, glycerol monooleate, other fatty acids and fatty acid esters with carbon chain lengths of C$_{12}$ to C$_{18}$, and combinations thereof.

31. A method of administering dextromethorphan to a subject in need thereof, the method comprising applying a transdermal delivery device to the skin of the subject, wherein the transdermal delivery device is configured to have a flux characteristic such that the applying transdermally delivers dextromethorphan about 2 mg/day to about 50 mg/day to the subject.

32. The method of embodiment C31, wherein the transdermal delivery device is configured to have a flux characteristic such that the applying transdermally delivers dextromethorphan about 5 mg/day to about 50 mg/day (e.g., about 5 mg/day, about 10 mg/day, about 20 mg/day, about 30 mg/day, about 40 mg/day, about 50 mg/day, or any ranges between the recited values) to the subject for 1 day or more (e.g., 1.5 days, 2 days, 3 days, 4 days, 5 days, 6 days, 7 days, or any ranges between the recited values).

EXAMPLES

Example 1. Preparation of Dextromethorphan
Transdermal Patch

This example shows one procedure for preparing dextromethorphan drug-in-adhesive patch. Dextromethorphan base is generally commercially available. Alternatively, dextromethorphan base can be prepared by conversion of dextromethorphan hydrobromide into the free base, for example, using a 1:1 molar ratio of NaOH.

Preparation of Formulation A, which uses acrylate adhesive with no skin permeation enhancers. In a 150-mL beaker was added in 10 g of ethyl acetate, followed by 2.5 g of DXM. The blend was mixed to dissolve the DXM. While mixing, it was added in acrylic PSA, 50 g of DuroTak 87-2287 (Henkel Adhesives) which has 50.5% of solids. Mixed the batch content for 30 minutes or till the content is homogeneous. The resulting wet solution was then casted onto a release liner (Loparex Corp.), using a casting applicator of 10 mils. The casting was dried in a forced-air oven at 80° C. for 10 min. After drying, the dried casting was laminated to a patch backing film, Scotchpak 1012 (3 M Drug Delivery Systems). The patch was die-cut into a 30 cm$^2$ shape. The resulting transdermal patch has adhesive matrix thickness of 2.5 mils (weighs about 180 mg of adhesive matrix per patch), and contains 9% DXM. HPLC analysis confirmed that a patch contains about 16 mg of DXM. The patch has good skin adhesion and adhered snugly on skin for more than 48 hours. The patch was die-cut to fix on the Franz cells for skin permeation study. No crystals were observed on the patch for 6 months at 25° C., indicating good stability of the transdermal patch formulation.

Preparation of Formulation B, which uses silicone adhesive with no skin permeation enhancers. In a 150-mL beaker was added in 10 g of ethyl acetate, followed by 2.5 g of DXM. The blend was mixed to dissolve the DXM. While mixing, it was added in silicone PSA, 50 g of Bio-PSA DC7-4502 (Dow Corning) which has 60.0% of solids. The batch content was mixed for 30 minutes or till the content is homogeneous. The resulting wet solution was casted onto a fluoropolymer-coated release liner (3M's 1022) using a casting applicator of 15 mils. The casting was dried in a forced-air oven at 80° C. for 10 min. After drying, the dried casting was laminated to a patch backing film, Scotchpak 1012 (3 M Drug Delivery Systems). The patch was die-cut into a 30 cm² shape. The resulting transdermal patch has adhesive matrix thickness of 3.5 mils. The patch has good skin adhesion and adhered snugly on skin for more than 48 hours. The patch was die-cut to fix on the Franz cells for skin permeation study. No crystals were observed on the patch for 6 months at 25° C., indicating good stability of the transdermal patch formulation.

Preparation of Formulation C, which uses a mixture of acrylate and silicone adhesive with no skin permeation enhancers, with the concentration of dextromethorphan being kept 9%. Following similar procedures above, three formulations were prepared, Formulation C1-C3, with a blend of silicone/acrylic PSA at a ratio of 54/46, 18/82, and 9/91, respectively.

Preparation of Formulation D, Following similar procedures above, formulations with various amounts of permeation enhancers are also prepared. Formulation D1 contains isopropyl myristate in an amount of 7.7%; Formulation D2 contains isopropyl myristate in an amount of 10%. As a control, Formulation DO was also prepared, which contains no isopropyl myristate.

The following table 1 summarizes the ingredients of different formulations prepared above, with weight percentages. (The percentages in the table refers to dry weight.)

TABLE 1

| Formulation No. | A | B | C1 | C2 | C3 | D0 | D1 | D2 |
|---|---|---|---|---|---|---|---|---|
| DXM | 9 | 8 | 9 | 9 | 9 | 10 | 10 | 10 |
| DuroTak 87-2287 | 91 | 92 | 49 | 16 | 8 | 90 | 82.3 | 80 |
| DC 7-4502 | | | 42 | 75 | 83 | | | |
| IPM | | | | | | 0 | 7.7 | 10 |
| Total | 100 | 100 | 100 | 100 | 100 | 100 | 100 | 100 |

Example 2. Transdermal Flux Test

Transdermal flux of Dextromethorphan from the patch was tested using human cadaver epidermis by Franz Diffusion Cell method.

Patch formulations A, B, and C prepared in Example 1 were used for a skin permeation study using the following protocol:

Franz cell assembly—Logan Instruments (6-cell unit)

Each cell has 12 mL volume, 1.5 cm diameter orifice

Receptor medium is a phosphate buffer solution (PBS) pH 7.4

Cell temperature is maintained at 37° C.

Sampling method: take 1.5 mL for HPLC assay, empty cell, replace with fresh medium Sampling time points: 4, 8, 12, 24 and 48 hours Cadaver skin is used and is obtained from New York Fire Fighters Skin Bank. Skin No. MM07116, While, Age 58, male, skin site: left posterior leg.

Assay method for media: HPLC based.

RESULTS of the study for Formulations A and B are presented in Table 1 below (See also FIG. 1). The values presented are cumulative amount of DXM permeated per cm² (i.e., µg/cm²).

TABLE 2

| | Formulation | |
| | A Acrylic PSA DuroTak 87-2287 | B Silicone PSA DC7-4502 |
| Hours | | |
|---|---|---|
| 0 | 0.0 | 0.0 |
| 4 | 48.6 | 25.8 |
| 8 | 124.9 | 79.8 |
| 12 | 201.3 | 138.1 |
| 24 | 424.3 | 294.4 |
| 48 | 625.1 | 597.0 |

RESULTS of the study for Formulations C1-C3 are presented in Table 3 below (See also FIG. 2). The values presented are cumulative amount of DXM permeated per cm² (i.e., µg/cm²).

TABLE 3

| | Formulation | | |
| | C1 | C2 | C3 |
| | | Sil:Acrylic ratio | |
| Day | 54/46 | 18/82 | 9/91 |
|---|---|---|---|
| 0.33 | 71.0 | 34.8 | 159.5 |
| 1 | 308.1 | 215.9 | 487.0 |
| 2 | 536.5 | 433.3 | 768.8 |
| 3 | 667.8 | 584.1 | 902.6 |
| 4 | 755.2 | 703.7 | 979.1 |
| 5 | 815.8 | 784.0 | 1023.5 |
| 6 | 866.3 | 854.6 | 1060.6 |
| 7 | 906.7 | 910.2 | 1086.1 |

Example 3. Dextromethorphan Transdermal Patch with Permeation Enhancers

Formulations D0-D2 were also tested for their in vitro flux characteristics following the same protocol as described in Example 2. The results were shown in Table 4 (see also FIG. 3).

TABLE 4

| Formulation | D0 | D1 | D2 |
|---|---|---|---|
| IPM % | 0 | 7.7 | 10.0 |
| 24-h flux | 141.3 | 240.0 | 334.6 |

The results clearly indicate that increased level of IPM, up to 10%, significantly enhance the skin permeation of DXM.

Example 4. In Vivo Pharmacokinetic Studies

This example concerns an open-label, randomized, two-treatment, two-period, two-sequence crossover study that was conducted with 16 healthy adult male and female subjects to evaluate the comparative bioavailability of a test dextromethorphan patch, 15 mg/24 hr relative to that of NUEDEXTA® (dextromethorphan hydrobromide and quinidine sulfate) capsules, 20 mg/10 mg (Avanir Pharmaceuticals, Inc.) under fasted conditions. The 16 subjects in this study were all genotyped to determine CYP2D6 genotype. All 16 subjects can be characterized as dextromethorphan extensive metabolizer. See e.g., Treducu A. L. D. et al. *Frontiers in Pharmacology, vol. 9, Article* 305 (April 2018).

The pharmacokinetic profile for both dextromethorphan and dextrorphan (one metabolite of dextromethorphan) were measured in this study.

In one period of the study, one (1) dextromethorphan patch, a 45 cm$^2$ patch with 35 mg DXM, which is a drug-in-adhesive patch, with the DIA layer containing about 80% by weight of an adhesive (Duro-Tak 87-2287), about 10% by weight of dextromethorphan base and about 10% by weight of permeation enhancer isopropyl myristate, which was designed to transdermally deliver about 15 mg/24 hr, was applied on the upper outer left arm of healthy subjects for 24 hours following an overnight fast of at least 10 hours. In the other study period, a single NUEDEXTA® (dextromethorphan hydrobromide and quinidine sulfate) capsule, 20 mg/10 mg, was administered every 12 hours (0 and 12 hours) (for a total dose of 40 mg/20 mg over a 24-hour period) following an overnight fast of at least 10 hours (0-hour).

For NUEDEXTA® treatment, the subjects were overnight fasted of at least 10 hours only prior to the 0-hour dose. The order of administration follows a two-sequence randomization schedule. Blood samples were collected pre-dose and at intervals over 96 hours after dosing (0-hour) with the study drug in each study period. Subjects were confined at the clinical facility from at least 10 hours before dosing (0-hour) until after the 36-hour blood sample collection in each study period and returned to the clinical facility for the 48-, 72- and 96-hour blood sample collections. The interval between doses (0-hour) were at least 10 days.

The plasma concentrations of dextromethorphan and its active metabolite dextrorphan were measured by a fully validated analytical procedure. Statistical analysis using average bioequivalence methodology was performed to evaluate the bioavailability of the test formulation relative to that of the reference product for dextromethorphan and dextrorphan only.

The study was designed based on the known pharmacokinetics of NUEDEXTA® (dextromethorphan hydrobromide and quinidine sulfate) Capsules, the FDA Draft Guidance on dextromethorphan hydrobromide and quinidine sulfate capsules, and generally accepted standards for the conduct of bioavailability/bioequivalence studies under fasted conditions and adhesion studies. To minimize any possibility of a carry-over effect, a washout period of at least 10 days was selected for this study.

The study was also designed to minimize potential drug-drug-interaction that may affect the results of this study. For example, the subjects were screened and monitored for taking drugs such as MAO inhibitors, tricyclic antidepressants, SSRIs, drugs that are implicated in TdP or cardiac arrhythmia, inducers or inhibitors of CYP3A4, or CYP2D6 etc.

Pharmacokinetic Results

Blood samples were collected at these time points (relative to dosing minute): Pre-dose (0-hour) and at 0.5, 1.0, 1.5, 2.0, 3.0, 4.0, 5.0, 6.0, 7.0, 9.0, 12.0, 13.0, 14.0, 15.0, 16.0, 17.0, 18.0, 20.0, 24.0, 24.5, 25.0, 26.0, 30.0, 36.0, 48.0*, 72.0* and 96.0* hours post-dose (* return sample). The samples were then processed and analyzed for both dextromethorphan and dextrophan concentrations using validated analytical methods. SAS®, Version 9.4 or higher was used for all pharmacokinetic and statistical calculations.

Tables 5A-5D show the results from this study. Tables A and C show the dextromethorphan and dextrophan plasma concentrations, respectively, in subjects orally administered Neudextra (Reference) twice a day. Tables B and D show the dextromethorphan and dextrophan plasma concentrations, respectively, in subjects treated with dextromethorphan patch for 24 hours.

TABLE 5A

| | | | | | | | | |
|---|---|---|---|---|---|---|---|---|
| | | | Dextromethorphan PK Profile in Subjects Treated Neudexta | | | | | |
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
| 2001 | 1 | 2 | 0.993 | 351.9471 | 349.606 | 184.0613 | 16.601 | 15 |
| 2002 | 2 | 1 | 0.964 | 195.315 | 188.2605 | 125.9288 | 10.095 | 18 |
| 2003 | 1 | 2 | 0.968 | 678.6678 | 657.1278 | 261.3503 | 18.961 | 15 |
| 2004 | 2 | 1 | 0.925 | 1179.091 | 1090.282 | 413.963 | 25.246 | 18 |
| 2005 | 1 | 2 | 0.985 | 241.7969 | 238.2765 | 139.581 | 10.527 | 16 |
| 2006 | 2 | 1 | 0.988 | 113.702 | 112.3683 | 71.981 | 5.179 | 18 |
| 2007 | 1 | 2 | 0.988 | 212.503 | 209.9133 | 120.7003 | 9.266 | 16 |
| 2008 | 2 | 1 | 0.987 | 199.7647 | 197.2488 | 115.1745 | 8.949 | 17 |
| 2009 | 1 | 2 | 0.977 | 61.9881 | 60.5778 | 41.9003 | 3.009 | 17 |
| 2010 | 2 | 1 | 0.992 | 420.076 | 416.5713 | 198.18 | 14.367 | 16 |
| 2011 | 2 | 1 | 0.991 | 146.6518 | 145.3553 | 94.6668 | 7.912 | 16 |
| 2012 | 1 | 2 | 0.987 | 630.2464 | 622.358 | 258.1298 | 17.371 | 18 |
| 2013 | 2 | 1 | 0.96 | 1127.656 | 1082.814 | 391.2635 | 27.377 | 17 |
| 2014 | 1 | 2 | 0.99 | 209.3143 | 207.2588 | 119.782 | 9.519 | 18 |
| 2015 | 2 | 1 | 0.989 | 203.16 | 200.8948 | 123.0515 | 11.967 | 15 |
| 2016 | 1 | 2 | 0.994 | 413.279 | 410.8915 | 188.3373 | 13.428 | 16 |
| N | | | 16 | 16 | 16 | 16 | 16 | 16 |
| Mean | | | 0.98 | 399.0725 | 386.8627 | 178.0032 | 13.1109 | 16.625 |
| St. Dev. | | | 0.0182 | 341.34 | 321.0667 | 106.3368 | 6.6888 | 1.1475 |
| CV(%) | | | 1.8534 | 85.5333 | 82.9924 | 59.7387 | 51.0169 | 6.902 |

TABLE 5A-continued

| | | | Dextromethorphan PK Profile in Subjects Treated Neudexta | | | | | |
|---|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
| Min. | | | 0.9247 | 61.9881 | 60.5778 | 41.9003 | 3.009 | 15 |
| Median | | | 0.9876 | 227.15 | 224.0949 | 132.7549 | 11.247 | 16.5 |
| Max. | | | 0.9942 | 1179.091 | 1090.282 | 413.963 | 27.377 | 18 |
| Geometric Mean | | | — | 293.6809 | 287.7623 | 151.5212 | 11.4739 | — |
| Geometric CV(%) | | | — | 96.1162 | 94.5644 | 65.4088 | 60.9954 | — |

TABLE 5B

| | | | Dextromethorphan PK Profile in Subjects Treated DXM Patch | | | | | | |
|---|---|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) | Kel (h-1) |
| 2001 | 2 | 2 | 0.995 | 343.5848 | 341.9338 | 225.8408 | 12.168 | 13 | 0.0521 |
| 2002 | 1 | 1 | 0.979 | 157.7533 | 154.4763 | 83.966 | 5.918 | 24 | 0.0598 |
| 2003 | 2 | 2 | 0.993 | 254.6006 | 252.7 | 138.4305 | 7.924 | 13 | 0.0558 |
| 2004 | 1 | 1 | 0.909 | 762.9419 | 693.3915 | 227.2223 | 15.069 | 25 | 0.028 |
| 2005 | 2 | 2 | 0.981 | 108.1344 | 106.0843 | 39.8225 | 3.565 | 24 | 0.0449 |
| 2006 | 1 | 1 | 0.976 | 155.7666 | 152.0265 | 76.285 | 5.39 | 24 | 0.0406 |
| 2007 | 2 | 2 | 0.974 | 76.1848 | 74.1835 | 37.4935 | 2.768 | 24 | 0.0655 |
| 2008 | 1 | 1 | 0.953 | 160.8027 | 153.2865 | 101.7265 | 5.729 | 9 | 0.089 |
| 2009 | 2 | 2 | 0.983 | 135.951 | 133.5808 | 60.496 | 5.299 | 24.5 | 0.0464 |
| 2010 | 1 | 1 | 0.989 | 170.5676 | 168.6183 | 93.6805 | 5.488 | 24.5 | 0.0487 |
| 2011 | 1 | 1 | 0.981 | 150.6617 | 147.8318 | 88.5355 | 5.359 | 13 | 0.0594 |
| 2012 | 2 | 2 | 0.991 | 175.1153 | 173.5208 | 89.2915 | 5.41 | 24 | 0.0583 |
| 2013 | 1 | 1 | 0.972 | 135.1146 | 131.3655 | 59.5475 | 5.058 | 24.5 | 0.0501 |
| 2014 | 2 | 2 | 0.988 | 103.1524 | 101.9025 | 51.8775 | 3.747 | 13 | 0.0448 |
| 2015 | 1 | 1 | 0.99 | 89.5274 | 88.629 | 49.1685 | 3.503 | 24.5 | 0.0601 |
| 2016 | 2 | 2 | 0.98 | 118.201 | 115.859 | 56.2235 | 3.982 | 24.5 | 0.0418 |
| N | | | 16 | 16 | 16 | 16 | 16 | 16 | 16 |
| Mean | | | 0.9771 | 193.6287 | 186.8369 | 92.4755 | 6.0236 | 20.5313 | 0.0528 |
| St. Dev. | | | 0.0208 | 165.2082 | 149.9839 | 58.4479 | 3.2516 | 5.8807 | 0.0135 |
| CV(%) | | | 2.1321 | 85.3221 | 80.2753 | 63.2036 | 53.9815 | 28.6425 | 25.5494 |
| Min. | | | 0.9088 | 76.1848 | 74.1835 | 37.4935 | 2.768 | 9 | 0.028 |
| Median | | | 0.9811 | 153.2141 | 149.9291 | 80.1255 | 5.3745 | 24 | 0.0511 |
| Max. | | | 0.9952 | 762.9419 | 693.3915 | 227.2223 | 15.069 | 25 | 0.089 |
| Geometric Mean | | | — | 160.6092 | 156.8942 | 79.6881 | 5.4375 | — | — |
| Geometric CV(%) | | | — | 60.1868 | 58.6836 | 58.0178 | 46.2616 | — | — |

TABLE 5C

| | | | Dextrorphan PK Profile in Subjects Treated Neudexta | | | | | |
|---|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
| 2001 | 1 | 2 | 0.91 | 54.6319 | 49.7395 | 37.0408 | 2.508 | 15 |
| 2002 | 2 | 1 | 0.95 | 54.7694 | 52.0113 | 44.3253 | 4.736 | 3 |
| 2003 | 1 | 2 | 0.79 | 44.4308 | 35.1195 | 19.2823 | 1.375 | 3 |
| 2004 | 2 | 1 | 0.758 | 45.5979 | 34.5633 | 16.5818 | 0.997 | 18 |
| 2005 | 1 | 2 | 0.933 | 49.1071 | 45.8165 | 37.2095 | 2.842 | 2 |
| 2006 | 2 | 1 | 0.846 | 21.7259 | 18.3733 | 17.4788 | 1.763 | 2 |
| 2007 | 1 | 2 | 0.923 | 34.5947 | 31.9278 | 25.6383 | 1.927 | 15 |
| 2008 | 2 | 1 | 0.863 | 27.3844 | 23.634 | 20.3403 | 1.463 | 3 |
| 2009 | 1 | 2 | 0.977 | 61.0768 | 59.6648 | 50.6268 | 4.251 | 16 |
| 2010 | 2 | 1 | 0.88 | 47.2853 | 41.614 | 29.7973 | 2.385 | 5 |
| 2011 | 2 | 1 | 0.944 | 44.4111 | 41.9088 | 38.2585 | 4.014 | 2 |
| 2012 | 1 | 2 | 0.773 | 35.9404 | 27.7748 | 18.5353 | 1.369 | 4 |
| 2013 | 2 | 1 | — | — | 24.2913 | 9.816 | 0.709 | 18 |
| 2014 | 1 | 2 | 0.907 | 33.6648 | 30.522 | 24.7718 | 1.804 | 3 |
| 2015 | 2 | 1 | 0.872 | 42.554 | 37.1155 | 29.618 | 2.482 | 2 |
| 2016 | 1 | 2 | 0.877 | 37.8946 | 33.2445 | 26.2825 | 2.035 | 4 |
| N | | | 15 | 15 | 16 | 16 | 16 | 16 |
| Mean | | | 0.8802 | 42.338 | 36.7075 | 27.8502 | 2.2913 | 7.1875 |

TABLE 5C-continued

| | | | Dextrorphan PK Profile in Subjects Treated Neudexta | | | | |
|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) |
| St. Dev. | | | 0.0657 | 10.6596 | 11.2148 | 11.1675 | 1.1676 | 6.5138 |
| CV(%) | | | 7.469 | 25.1775 | 30.5518 | 40.0985 | 50.9602 | 90.6263 |
| Min. | | | 0.758 | 21.7259 | 18.3733 | 9.816 | 0.709 | 2 |
| Median | | | 0.8801 | 44.4111 | 34.8414 | 25.9604 | 1.981 | 3.5 |
| Max. | | | 0.9769 | 61.0768 | 59.6648 | 50.6268 | 4.736 | 18 |
| Geometric Mean | | | — | 40.9614 | 35.0859 | 25.6926 | 2.0294 | — |
| Geometric CV(%) | | | — | 28.0586 | 32.3114 | 44.7726 | 55.4075 | — |

TABLE 5D

| | | | | Dextrorphan PK Profile in Subjects Treated DXM Patch | | | | | |
|---|---|---|---|---|---|---|---|---|---|
| Sub. | Per. | Seq. | AUC 0-t/ AUC 0-∞ | AUC 0-∞ | AUC 0-t (h · ng/mL) | AUC 0-24 | Cmax (ng/mL) | Tmax (h) | Kel (h-1) |
| 2001 | 2 | 2 | 0.816 | 23.5515 | 19.2253 | 9.77 | 0.665 | 26 | 0.0495 |
| 2002 | 1 | 1 | — | — | 13.3518 | 7.81 | 0.658 | 13 | — |
| 2003 | 2 | 2 | 0.786 | 15.0118 | 11.7988 | 7.563 | 0.478 | 20 | 0.071 |
| 2004 | 1 | 1 | — | — | 16.3933 | 6.348 | 0.58 | 24.5 | — |
| 2005 | 2 | 2 | — | — | 1.5003 | 0 | 0.279 | 30 | — |
| 2007 | 2 | 2 | — | — | 2.594 | 0.955 | 0.286 | 30 | — |
| 2008 | 1 | 1 | — | — | 7.8075 | 5.6295 | 0.431 | 24 | — |
| 2009 | 2 | 2 | — | — | 4.7703 | 3.265 | 0.354 | 12 | — |
| 2010 | 1 | 1 | — | — | 11.3405 | 6.759 | 0.539 | 26 | — |
| 2011 | 1 | 1 | — | — | 1.6505 | 1.102 | 0.312 | 26 | — |
| 2012 | 2 | 2 | — | — | 4.957 | 2.741 | 0.401 | 24 | — |
| 2013 | 1 | 1 | — | — | 13.1663 | 6.377 | 0.683 | 24 | — |
| 2014 | 2 | 2 | — | — | 6.6303 | 4.4165 | 0.393 | 26 | — |
| 2015 | 1 | 1 | — | — | 10.327 | 5.9315 | 0.588 | 14 | — |
| 2016 | 2 | 2 | — | — | 4.1193 | 2.386 | 0.319 | 26 | — |
| N | | | 2 | 2 | 15 | 15 | 15 | 15 | 2 |
| Mean | | | 0.8011 | 19.2816 | 8.6421 | 4.7369 | 0.4644 | 23.0333 | 0.0602 |
| St. Dev. | | | 0.0215 | 6.0384 | 5.5101 | 2.8797 | 0.1446 | 5.7273 | 0.0152 |
| CV(%) | | | 2.6783 | 31.317 | 63.7586 | 60.7921 | 31.1453 | 24.8654 | 25.2412 |
| Min. | | | 0.786 | 15.0118 | 1.5003 | 0 | 0.279 | 12 | 0.0495 |
| Median | | | 0.8011 | 19.2816 | 7.8075 | 5.6295 | 0.431 | 24.5 | 0.0602 |
| Max. | | | 0.8163 | 23.5515 | 19.2253 | 9.77 | 0.683 | 30 | 0.071 |
| Geometric Mean | | | — | 18.8029 | 6.7033 | 4.1953 | 0.4433 | — | — |
| Geometric CV(%) | | | — | 32.6691 | 96.3776 | 82.6752 | 32.64 | — | — |

Based on this study, it was also unexpectedly found that for subjects treated with DXM patch, the ratios of $AUC_{0\text{-}24}$, $AUC_{0\text{-}t}$, and $C_{max}$ of DXM to DRP observed for the patch treatment were significantly higher than the respective ratios observed for the Neudexta treatment. For example, the mean ratio of $AUC_{0\text{-}24}$ of DXM to DRP observed for the patch treatment is close to 3× of that observed for Neudexta treatment (24.54:9.03), see table 6 below.

TABLE 6

| | | | Comparison of PK Profiles for Patch Neudexta Treatments | | | | | | | |
|---|---|---|---|---|---|---|---|---|---|---|
| | | Neudexta Treatment | | | | | Patch Treatment | | | |
| Sub. | Per. | Seq. | AUC 0-t (DXM/ DRP) | AUC 0-24 (DXM/ DRP) | Cmax (DXM/ DRP) | Per. | Seq. | AUC 0-t (DXM/ DRP) | AUC 0-24 (DXM/ DRP) | Cmax (DXM/ DRP) |
| 2001 | 1 | 2 | 7.03 | 4.97 | 6.62 | 2 | 2 | 17.79 | 23.12 | 18.30 |
| 2002 | 2 | 1 | 3.62 | 2.84 | 2.13 | 1 | 1 | 11.57 | 10.75 | 8.99 |
| 2003 | 1 | 2 | 18.71 | 13.55 | 13.79 | 2 | 2 | 21.42 | 18.30 | 16.58 |
| 2004 | 2 | 1 | 31.54 | 24.96 | 25.32 | 1 | 1 | 42.30 | 35.79 | 25.98 |
| 2005 | 1 | 2 | 5.20 | 3.75 | 3.70 | 2 | 2 | 70.71 | — | 12.78 |
| 2006 | 2 | 1 | 6.12 | 4.12 | 2.94 | 1 | 1 | — | — | — |
| 2007 | 1 | 2 | 6.57 | 4.71 | 4.81 | 2 | 2 | 28.60 | 39.26 | 9.68 |
| 2008 | 2 | 1 | 8.35 | 5.66 | 6.12 | 1 | 1 | 19.63 | 18.07 | 13.29 |
| 2009 | 1 | 2 | 1.02 | 0.83 | 0.71 | 2 | 2 | 28.00 | 18.53 | 14.97 |
| 2010 | 2 | 1 | 10.01 | 6.65 | 6.02 | 1 | 1 | 14.87 | 13.86 | 10.18 |
| 2011 | 2 | 1 | 3.47 | 2.47 | 1.97 | 1 | 1 | 89.57 | 80.34 | 17.18 |
| 2012 | 1 | 2 | 22.41 | 13.93 | 12.69 | 2 | 2 | 35.01 | 32.58 | 13.49 |
| 2013 | 2 | 1 | 44.58 | 39.86 | 38.61 | 1 | 1 | 9.98 | 9.34 | 7.41 |

TABLE 6-continued

Comparison of PK Profiles for Patch Neudexta Treatments

| | | | Neudexta Treatment | | | | | Patch Treatment | | |
|---|---|---|---|---|---|---|---|---|---|---|
| Sub. | Per. | Seq. | AUC 0-t (DXM/ DRP) | AUC 0-24 (DXM/ DRP) | Cmax (DXM/ DRP) | Per. | Seq. | AUC 0-t (DXM/ DRP) | AUC 0-24 (DXM/ DRP) | Cmax (DXM/ DRP) |
| 2014 | 1 | 2 | 6.79 | 4.84 | 5.28 | 2 | 2 | 15.37 | 11.75 | 9.53 |
| 2015 | 2 | 1 | 5.41 | 4.15 | 4.82 | 1 | 1 | 8.58 | 8.29 | 5.96 |
| 2016 | 1 | 2 | 12.36 | 7.17 | 6.60 | 2 | 2 | 28.13 | 23.56 | 12.48 |
| N | | | 16 | 16 | 16 | | | 15 | 16 | |
| Mean | | | 12.07 | 9.03 | 8.88 | | | 29.43 | 24.54 | 13.12 |
| St. Dev. | | | 11.78 | 10.15 | 9.96 | | | 22.93 | 18.82 | 5.06 |
| CV(%) | | | 97.60% | 112.45% | 112.10% | | | 77.89% | 76.70% | 38.60% |

FIGS. 4A and 4B show the graph of dextromethorphan and dextrorphan concentrations from 0-96 hours.

Example 5. Multilayer Patch Design

In this example, a novel multilayer design is described.

As shown in FIG. 5, an exemplary patch design useful for the embodiments herein can include a contact layer and a reservoir layer. The contact layer (top layer in FIG. 5) can have the following ingredients: 1) an Adhesive (e.g., DURO-TAK 287-2287): about 77.5%-about 75%; 2) Drug (Dextromethorphan base): about 10%; 3) Enhancer (e.g., Isopropyl Myristate—IPM): about 10%; and 4) a Kollidon, e.g., KollidonVA64: about 2.5%-about 5%. The reservoir layer can have the following ingredients: 1) an Adhesive (e.g., DURO-TAK 287-2287): about 57.5%-about 20%; 2) Drug (Dextromethorphan base): about 30%-about 50%; 3) Enhancer (e.g., Isopropyl Myristate—IPM): about 10%; and 4) a Kollidon e.g., Kollidon VA64: about 2.5%-about 20%. The bottom layer can be a backing layer or can be an adhesive layer such as the same as the top layer. Suitable backing layers are described herein. Kollidon is a brand-name which refers to a vinylpyrrolidone polymer (e.g., a vinylpyrrolidone-vinyl acetate copolymers, e.g., Kollidon VA64). Prior to application, the contact layer is typically protected with a release liner. Suitable release liners are also described herein.

In one example, the multilayer patch can have a size of 60 cm² or more, e.g., about 60 cm² to about 150 cm².

In one example, the multilayer patch can have a size of 70 cm², which is designed to contain a total of about 370 mg dextromethorphan base. Such patch is suitable for application for 7 days, which can transdermally deliver about 20 mg or more of dextromethorphan per day for 7 days (total delivery approximately 140 mg or more) over 7 days).

Example 6. Pharmacokinetic Simulation

This example shows a simulation of Dextromethorphan (DXM or DM) and Dextrorphan (DOR) Plasma Profiles over 7 days following daily application of different sized patches.

The method used to simulate the plasma profile after daily dosing over 7 days for patches of different sizes is called superposition. This involves repetitively adding concentration of next dose to the profile of the previous dose, without the need for any compartmental modeling, or the need to know any PK parameters. First, Dextromethorphan (abbreviated as DXM or DM) and Dextrorphan (abbreviated as DOR or DRP) mean plasma profiles after a single 24 hr application of a 70 cm² patch was obtained with a 45 cm² patch as shown in Example 4. The assumptions are that the absorption rate of DXM is proportionally increased with patch size, while DXM to DRP conversion rate, DXM clearance rate, and DRP clearance rate were not changed.

Then, DXM and DRP plasma profiles from a 60 cm² and 90 cm² patch with once-a-day application for 7 days were predicted using the predicted single dose profiles and the superposition principle, with the assumptions that each subsequent dosing after Day 1 will not cause changes in the clearance of DXM, DRP and conversion of DXM and DRP.

The pharmacokinetic simulation results are shown in FIGS. 6A-6D. As shown in FIG. 6B, daily administration of a DXM patch with a size of about 60 cm² and above will produce a DXM plasma level falling within the peak and trough of the DXM concentration from oral administration of Neudexta BID (20 mg DXM/10 mg quinidine) for 7 days. Moreover, the DXM plasma level obtained from daily administration of DXM patches are less variable, with the peak to trough ratio lower than those observed from oral administration of Neudexta BID (20 mg DXM/10 mg quinidine) for 7 days.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. A method of treating a neurological disorder in a subject in need thereof, the method comprising applying a transdermal delivery device to the skin of the subject once daily, wherein the transdermal delivery device comprises an adhesive layer comprising an adhesive in the amount of about 65% to about 85%, dextromethorphan in an amount of about 2% to about 12%, a permeation enhancer in an amount of about 6% to about 12%, and optional other ingredients in an amount of about 0% to about 20%, wherein the transdermal delivery device is configured to provide dextromethorphan about 15 mg/day to about 40 mg/day to the subject, wherein the subject is not co-administered a CYP2D6 inhibitor, and wherein the neurological disorder is depression, stroke, traumatic brain injury, seizure, methotrexate neurotoxicity, Parkinson's disease, autism, Alzheimer's disease, or a combination thereof, wherein the permeation enhancer is isopropyl myristate, wherein dextromethorphan is the only active agent in the transdermal delivery device, and wherein the subject does not suffer from a cough and/or does not need an antitussive, wherein the subject is a human subject and the applying results in one or more of the following pharmacokinetic profile in the human subject:

a. a mean $C_{max}$ of dextromethorphan of about 3 ng/ml to about 12 ng/ml at day 1 post application;

b. a mean $AUC_{0-24}$ of dextromethorphan of about 40 ng*h/ml to about 150 ng*h/ml at day 1 post application;

c. a mean ratio of $C_{24h}/C_{12h}$ of dextromethorphan of about 1 to about 1.5 at day 1 post application;

d. a mean ratio of $C_{24h}/C_{6h}$ of dextromethorphan of about 1.5 to about 2.5 at day 1 post application;

e. a mean ratio of $C_{24h}/C_{18h}$ of dextromethorphan of about 0.85 to about 1.3 at day 1 post application;

f. a mean $C_{max}$ of dextrorphan of not more than 2 ng/ml at day 1 post application;

g. a mean $AUC_{0-24}$ of dextrorphan of not more than 10 ng*h/ml at day 1 post application;

h. a mean ratio of $C_{max}$ of dextromethorphan to $C_{max}$ of dextrophan of at least about 5 at day 1 post application; and i. a mean ratio of $AUC_{0-24}$ of dextromethorphan to $AUC_{0-24}$ of dextrophan of at least about 5 at day 1 post application.

2. The method of claim 1, wherein the isopropyl myristate is in an amount of about 10% of the adhesive layer.

3. The method of claim 1, wherein the subject is an extensive metabolizer of dextromethorphan.

4. The method of claim 1, wherein the subject is a poor metabolizer of dextromethorphan.

5. The method of claim 1, wherein the subject is sensitive to or otherwise intolerant to quinidine.

6. The method of claim 2, wherein the subject is an extensive metabolizer of dextromethorphan.

7. The method of claim 2, wherein the subject is a poor metabolizer of dextromethorphan.

8. The method of claim 2, wherein the subject is sensitive to or otherwise intolerant to quinidine.

* * * * *